(12) United States Patent (10) Patent No.: US 8,507,559 B2
Carter et al. (45) Date of Patent: Aug. 13, 2013

(54) CYCLOHEXENYL MODULATORS OF CHEMOKINE RECEPTOR ACTIVITY

(75) Inventors: Percy H. Carter, Princeton, NJ (US); Gregory D. Brown, Landsdale, PA (US); George V. De Lucca, Pennington, NJ (US); Douglas G. Batt, Wilmington, DE (US); Rui-Qin Liu, Belle Mead, NJ (US); Feng Qiu, Doylestown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 256 days.

(21) Appl. No.: 13/003,780

(22) PCT Filed: Jul. 14, 2009

(86) PCT No.: PCT/US2009/050449
§ 371 (c)(1),
(2), (4) Date: Jan. 12, 2011

(87) PCT Pub. No.: WO2010/009068
PCT Pub. Date: Jan. 21, 2010

(65) Prior Publication Data
US 2011/0118354 A1 May 19, 2011

Related U.S. Application Data

(60) Provisional application No. 61/081,180, filed on Jul. 16, 2008.

(51) Int. Cl.
*A01N 37/10* (2006.01)
*A01N 45/00* (2006.01)
*A61K 31/19* (2006.01)
*A61K 31/56* (2006.01)

(52) U.S. Cl.
USPC .......................................... 514/568; 514/170

(58) Field of Classification Search
USPC ................................................ 514/568, 170
See application file for complete search history.

(56) References Cited

U.S. PATENT DOCUMENTS

| 5,478,836 | A | 12/1995 | Müller et al. |
| 6,432,981 | B1 | 8/2002 | Finke et al. |
| 6,479,671 | B1 | 11/2002 | Konoike et al. |
| 6,984,642 | B1 | 1/2006 | Bischoff et al. |

FOREIGN PATENT DOCUMENTS

| WO | WO 99/46991 | 9/1999 |
| WO | WO 2004/110376 | 12/2004 |

OTHER PUBLICATIONS

Deno (Journal of the American Chemical Society (1950) 72:4057-4059).*
Ito et. al. (Cancer Science (2003) 94:3-8).*

Zlotnik, A. et al., "Chemokines: A New Classification System and Their Role in Immunity", Immunity, vol. 12, pp. 127-127 (2000).
Abbadie, C. et al., "Impaired neuropathic pain responses in mice lacking the chemokine receptor CCR2", Proceedings of the National Academy of Sciences, vol. 100, No. 13, pp. 7947-7952 (2003).
Abdi, R. et al., "Differential Role of CCR2 in Islet and Heart Allograft Rejection: Tissue Specificity of Chemokine/Chemokine Receptor Function in Vivo", The Journal of Immunology, vol. 172, pp. 767-775 (2004).
Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1+ Lymphocyte-Associated Th2-Type Immune Response in the Intestine", The Journal of Immunology, vol. 164, pp. 6303-6312 (2000).
Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).
Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).
Bachmann, W.E. et al., "The Diels-Alder Reaction of 1-Vinylnaphthalene with α,β- and α,β,γ,δ-Unsaturated Acids and Derivatives", Journal of the American Chemical Society, vol. 71, pp. 3062-3072 (1949).
Battistini, C. et al., "Nucleophilic Step of Ring-Opening Reactions of Cyclopropanes with Electrophiles. Electronic Substituent Effects on Stereoselectivity of Reactions of Some 1-Arylbicyclo[4.1.0]heptanes with Mercuric Salts", J. Org. Chem., vol. 43, No. 7, pp. 1400-1404 (1978).

(Continued)

*Primary Examiner* — Marcos Sznaidman
(74) *Attorney, Agent, or Firm* — Jing G. Sun; Terence J. Bogie

(57) ABSTRACT

The present application describes modulators of MCP-1 or CCR-2 of formula, (I) or stereoisomers or prodrugs or pharmaceutically acceptable salts thereof, wherein T, W, X, Y, Z, $R^1$, $R^2$, $R^4$ and $R^6$, are defined herein. In addition, methods of treating and preventing inflammatory diseases such as asthma and allergic diseases, as well as autoimmune pathologies such as rheumatoid arthritis and transplant rejection using modulators of formula, (I) are disclosed.

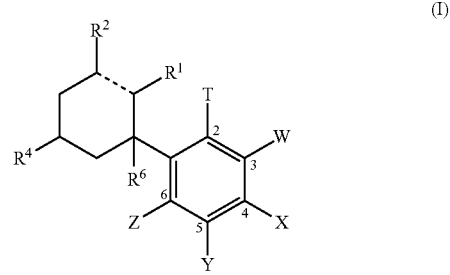

(I)

16 Claims, No Drawings

(56) References Cited

OTHER PUBLICATIONS

Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).
Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).
Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).
Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).
Carter, P.H., "Chemokine receptor antagonism as an approach to anti-inflammatory therapy: 'just right' or plain wrong?", Current Opinion in Chemical Biology, vol. 6, pp. 510-525 (2002).
Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).
Charo, I.F. et al., "The Many Roles of Chemokines and Chemokine Receptors in Inflammation", The New England Journal of Medicine, vol. 354, No. 6, pp. 610-621 (2006).
Cheng, J.-F. et al., "Novel Chromene Derivatives as TNF-α Inhibitors", Bioorganic & Medicinal Chemistry Letters, vol. 13, pp. 3647-3650 (2003).
Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).
Combadiere, C. et al., "Cloning and Functional Expression of a Human Eosinophil CC Chemokine Receptor", The Journal of Biological Chemistry, vol. 270, No. 27, pp. 16491-16494 (1995).
Connor, R.I. et al., "Change in Coreceptor Use Correlates with Disease Progression in HIV-1-Infected Individuals", J. Exp. Med., vol. 185, No. 4, pp. 621-628 (1997).
Connor, S.J. et al., "CCR2 expressing CD4+ lymphocytes are preferentially recruited to the ileum in Crohn's disease", Gut, vol. 53, pp. 1287-1294 (2004).
Conti, I. et al., "CCL2 (monocyte chemoattractant protein-1) and cancer", Seminars in Cancer Biology, vol. 14, pp. 149-154 (2004).
Craig, M.J. et al., "CCL2 (Monocyte Chemoattractant Protein-1) in cancer bone metastases", Cancer Metastasis Rev., vol. 25, pp. 611-619 (2006).
Crane, S.N. et al., "β-Substituted Cyclohexanecarboxamide: A Nonpeptidic Framework for the Design of Potent Inhibitors of Cathepsin K", Journal of Medicinal Chemistry, vol. 49, No. 3, pp. 1066-1079 (2006).
Dawson, J. et al., "Targeting monocyte chemoattractant protein-1 signalling in disease", Expert Opin. Ther. Targets, vol. 7, No. 1, pp. 35-48 (2003).
Deleuran, M. et al., "Localization of monocyte chemotactic and activating factor (MCAF/MCP-1) in psoriasis", Journal of Dermatological Science, vol. 13, pp. 228-236 (1996).
Deno, N.C., "The Diels-Alder Reaction α,β,γ,δ-Unsaturated Acids", Journal of the American Chemical Society, vol. 72, pp. 4057-4059 (1950).
Dimitrijevic, O.B. et al., "Absence of the Chemokine Receptor CCR2 Protects Against Cerebral Ischemia/Reperfusion Injury in Mice", Stroke, vol. 38, pp. 1345-1353 (2007).
Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).
Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).

Feria, M. et al., "The CCR2 receptor as a therapeutic target", Expert Opin. Ther. Patents, vol. 16, No. 1, pp. 49-57 (2006).
Ferreira, A.M. et al., "Diminished Induction of Skin Fibrosis in Mice with MCP-1 Deficiency", Journal of Investigative Dermatology, vol. 126, pp. 1900-1908 (2006).
Frangogiannis, N.G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).
Gao, Z. et al., "Unraveling the Chemistry of Chemokine Receptor Ligands", Chemical Reviews, vol. 103, No. 9, pp. 3733-3752 (2003).
Gharaee-Kermani, M. et al., "CC-chemokine receptor 2 required for bleomycin-induced pulmonary fibrosis", Cytokine, vol. 24, pp. 266-276 (2003).
Giles, R. et al., "Can We Target the Chemokine Network for Cancer Therapeutics?", Current Cancer Drug Targets, vol. 6, No. 8, pp. 659-670 (2006).
Gillitzer, R. et al., "MCP-1 mRNA Expression in Basal Keratinocytes of Psoriatic Lesions", The Journal of Investigative Dermatology, vol. 101, No. 2, pp. 127-131 (1993).
Gonzalo, J.-A. et al., "The Coordinated Action of CC Chemokines in the Lung Orchestrates Allergic Inflammation and Airway Hyperresponsiveness", J. Exp. Med., vol. 188, No. 1, pp. 157-167 (1998).
Grimm, M.C. et al., "Enhanced expression and production of monocyte chemoattractant protein-1 in inflammatory bowel disease mucosa", Journal of Leukocyte Biology, vol. 59, pp. 804-812 (1996).
Hasegawa, H. et al., "Antagonist of Monocyte Chemoattractant Protein 1 Ameliorates the Initiation and Progression of Lupus Nephritis and Renal Vasculitis in MRL/lpr Mice", Arthritis & Rheumatism, vol. 48, No. 9, pp. 2555-2566 (2003).
Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).
Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).
Horuk, R., "Molecular properties of the chemokine receptor family", Trends in Pharmacological Sciences, vol. 15, pp. 159-165 (1994).
Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).
Hughes, P.M. et al., "Monocyte Chemoattractant Protein-1 Deficiency is Protective in a Murine Stroke Model", Journal of Cerebral Blood Flow & Metabolism, vol. 22, No. 3, pp. 308-317 (2002).
Ishizuka, N. et al., "Structure-Activity Relationships of a Novel Class of Endothelin—A Receptor Antagonists and Discovery of Potent and Selective Receptor Antagonist, 2-(Benzo[1,3]dioxol-5-yl)-6-isopropyloxy-4-(4-methoxyphenyl)-2H-chromene-3-carboxylic acid (S-1255). 1. Study on Structure-Activity Relationships and Basic Structure Crucial for $ET_A$ Antagonism", Journal of Medicinal Chemistry, vol. 45, No. 10, pp. 2041-2055 (2002).
Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).
Karpus, W.J. et al., "An Important Role for the Chemokine Macrophage Inflammatory Protein-1α in the Pathogenesis of the T Cell-Mediated Autoimmune Disease, Experimental Autoimmune Encephalomyelitis", The Journal of Immunology, vol. 155, pp. 5003-5010 (1995).
Karrer, S. et al., "The -2518 Promotor Polymorphism in the MCP-1 Gene is Associated with Systemic Sclerosis", The Journal of Investigative Dermatology, vol. 124, vol. 1, pp. 92-98 (2005).
Kasama, T. et al., "Interleukin-10 Expression and Chemokine Regulation During the Evolution of Murine Type II Collagen-Induced Arthritis", J. Clin. Invest., vol. 95, pp. 2868-2876 (1995).
Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).

Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).

Kim, W.J.H. et al., "MCP-1 deficiency is associated with reduced intimal hyperplasia after arterial injury", Biochemical and Biophysical Research Communications, vol. 310, pp. 936-942 (2003).

Kitagawa, K. et al., "Blockade of CCR2 Ameliorates Progressive Fibrosis in Kidney", American Journal of Pathology, vol. 165, No. 1, pp. 237-246 (2004).

Koch, A.E. et al., "Macrophage Inflammatory Protein-1α. A Novel Chemotactic Cytokine for Macrophages in Rheumatoid Arthritis", J. Clin. Invest., vol. 93, pp. 921-928 (1994).

Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).

Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).

Lee, I. et al., "Blocking the Monocyte Chemoattractant Protein-1/CCR2 Chemokine Pathway Induces Permanent Survival of Islet Allografts through a Programmed Death-1 Ligand-1-Dependent Mechanism", The Journal of Immunology, vol. 171, pp. 6929-6935 (2003).

Lee, S.C. et al., "Cutaneous Injection of Human Subjects with Macrophage Inflammatory Protein-1α Induces Significant Recruitment of Neutrophils and Monocytes", vol. 164, pp. 3392-3401 (2000).

Liu, T. et al., "Depletion of macrophages reduces axonal degeneration and hyperalgesia following nerve injury", Pain, vol. 86, pp. 25-32 (2000).

Lloyd, C.M. et al., "RANTES and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and Invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of TER1, a Chemokine Receptor-Like Gene Expressed by Lymphoid Tissues", The Journal of Immunology, vol. 157, pp. 2759-2763 (1996).

Neote, K. et al., "Molecular Cloning, Functional Expression, and Signaling Characteristics of a C-C Chemokine Receptor", Cell, vol. 72, pp. 415-425 (1993).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pease, J.E. et al., "CCR1 antagonists in clinical development", Expert Opin. Investig. Drugs, vol. 14, No. 7, pp. 785-796 (2005).

Pérez de Lema, G. et al., "Chemokine Receptor Ccr2 Deficiency Reduces Renal Disease and Prolongs Survival in MRL/lpr Lupus-Prone Mice", Journal of the American Society of Nephrology, vol. 16, pp. 3592-3601 (2005).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rollins, B.J., "Chemokines", Blood, vol. 90, No. 3, pp. 909-928 (1997).

Ropp, G.A. et al., "Reactions of 1-(p-Bromophenyl)-1,3-butadiene and 1-(p-Nitrophenyl)-1,3-butadiene with Acrylic Acid and Ethyl Acetate", Journal of the American Chemical Society, vol. 72, pp. 3960-3963 (1950).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samson, M. et al., "Molecular Cloning and Functional Expression of a New Human CC-Chemokine Receptor Gene", Biochemistry, vol. 35, No. 11, pp. 3362-3367 (1996).

Saunders, J. et al., "Opportunities for novel therapeutic agents acting at chemokine receptors", Drug Discovery Today, vol. 4, No. 2, pp. 80-92 (1999).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 and online data supplement (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/lpr mice", Rheumatology, vol. 43, pp. 1121-1128 (2004).

Smith, M.W. et al., "Contrasting Genetic Influence of CCR2 and CCR5 Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

Sprague, P.W. et al., "Synthesis and Antiinflammatory Activity of cis-4,5,6,7,8,8a,9-Hexahydro-α-methyl-5-H-fluorene-2-acetic Acid", Journal of Medicinal Chemistry, vol. 20, No. 5, pp. 726-728 (1977).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-Fas$^{lpr}$ Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Wells, T.N.C. et al., "Plagiarism of the host immune system: lessons about chemokine immunology from viruses", Current Opinion in Biotechnology, vol. 8, pp. 741-748 (1997).

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshie, O. et al., "Novel lymphocyte-specific CC chemokines and their receptors", Journal of Leukocyte Biology, vol. 62, pp. 634-644 (1997).

\* cited by examiner

CYCLOHEXENYL MODULATORS OF CHEMOKINE RECEPTOR ACTIVITY

CROSS-REFERENCE TO RELATED APPLICATION

This application claims priority benefit to U.S. Provisional Application Ser. No. 61/081,180, filed on Jul. 16, 2008, the contents of which are herein incorporated by reference in its entirety.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, New Eng. J. Med. 1998, 338, 436-445 and Rollins, Blood 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, Trends Pharm. Sci. 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., Immunity 2000, 12, 121): CCR-1 (or "CKR-1" or "CC-CKR-1") [MIP-1α, MCP-3, MCP-4, RANTES] (Neote et al., Cell 1993, 72, 415-425, and Luster, New Eng. J. Med. 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA 1994, 91, 2752-2756, and Luster, New Eng. J. Med. 1998, 338, 436-445); CCR-3 (or "CKR-3" or "CC-CKR-3") [eotaxin-1, eotaxin-2, RANTES, MCP-3, MCP-4] (Combadiere et al., J. Biol. Chem. 1995, 270, 16491-16494, and Luster, New Eng. J. Med. 1998, 338, 436-445); CCR-4 (or "CKR-4" or "CC-CKR-4") [TARC, MDC] (Power et al., J. Biol. Chem. 1995, 270, 19495-19500, and Luster, New Eng. J. Med. 1998, 338, 436-445); CCR-5 (or "CKR-5" OR "CC-CKR-5") [MIP-1α, RANTES, MIP-1β] (Samson et al., Biochemistry 1996, 35, 3362-3367); CCR-6 (or "CKR-6" or "CC-CKR-6") [LARC] (Baba et al., J. Biol. Chem. 1997, 272, 14893-14898); CCR-7 (or "CKR-7" or "CC-CKR-7") [ELC] (Yoshie et al., J. Leukoc. Biol. 1997, 62, 634-644); CCR-8 (or "CKR-8" or "CC-CKR-8") [1-309] (Napolitano et al., J. Immunol., 1996, 157, 2759-2763); CCR-10 (or "CKR-10" or "CC-CKR-10") [MCP-1, MCP-3] (Bonini et al., DNA Cell Biol. 1997, 16, 1249-1256); and CCR-11 [MCP-1, MCP-2, and MCP-4] (Schweickart et al., J. Biol. Chem. 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells et al., Curr. Opin. Biotech. 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., Curr. Opin. Chem. Biol. 2002, 6, 510; Trivedi et al., Ann. Reports Med. Chem. 2000, 35, 191; Saunders et al., Drug Disc. Today 1999, 4, 80; Premack et al., Nature Medicine 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., J. Immun. 2000, 164, 3392-3401).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo et al., New Eng. J. Med. 2006, 354, 610-621; Gao, Z. et al., Chem. Rev. 2003, 103, 3733; Carter, P. H., Curr. Opin. Chem. Biol. 2002, 6, 510; Trivedi et al., Ann. Reports Med. Chem. 2000, 35, 191; Saunders et al., Drug Disc. Today 1999, 4, 80; Premack et al., Nature Medicine 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1−/−mice were unable to recruit monocytes into sites of inflammation after several different types of immune challenge (Lu, B. et al., *J. Exp. Med.* 1998, 187, 601). Likewise, CCR-2−/− mice were unable to recruit monocytes or produce interferon-γ when challenged with various exogenous agents; moreover, the leukocytes of CCR-2 null mice did not migrate in response to MCP-1 (Boring, L. et al., *J. Clin. Invest.* 1997, 100, 2552), thereby demonstrating the specificity of the MCP-1/CCR-2 interaction. Two other groups have independently reported equivalent results with different strains of CCR-2−/− mice (Kuziel, W. A. et al., *Proc. Natl. Acad. Sci. USA* 1997, 94, 12053, and Kurihara, T. et al., *J. Exp. Med.* 1997, 186, 1757). The viability and generally normal health of the MCP-1−/− and CCR-2−/−animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: Feria, M. et al., *Exp. Opin. Ther. Patents* 2006, 16, 49; and Dawson, J. et al., *Exp. Opin. Ther. Targets* 2003, 7, 35). This hypothesis has now been validated in a number of different animal disease models, as described below.

It is known that MIP-1α is elevated in the synovial fluid and blood of patients with rheumatoid arthritis (Koch, A. et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. et al., *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It is known that MCP-1 is upregulated in patients who develop bronchiolitis obliterans syndrome after lung transplantation (Reynaud-Gaubert, M. et al., *J. Heart Lung Transplant.,* 2002, 21, 721-730; Belperio, B. et al., *J. Clin. Invest.* 2001, 108, 547-556). In a murine model of bronchiolitis obliterans syndrome, administration of an antibody to MCP-1 led to attenuation of airway obliteration; likewise, CCR2−/− mice were resistant to airway obliteration in this same model (Belperio, J. et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (Lee, I. et al., *J. Immunol.* 2003, 171, 6929; Abdi, R. et al., *J. Immunol.* 2004, 172, 767). In rat graft models, CCR2 and MCP-1 was shown to be upregulated in grafts that develop graft vasculopathy (Horiguchi, K. et al., *J. Heart Lung Transplant.* 2002, 21, 1090). In another study, anti-MCP-1 gene therapy attenuated graft vasculopathy (Saiura, A. et al., *Arterioscler. Thromb. Vasc. Biol.* 2004, 24, 1886). One study described inhibition of experimental vein graft neointimal formation by blockage of MCP-1 (Tatewaki, H. et al., *J. Vasc. Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Gonzalo, J-A. et al., *J. Exp. Med.* 1998, 188, 157). It proved possible to reduce allergic airway inflammation in *Schistosoma mansoni* egg-challenged mice through the administration of antibodies for MCP-1 (Lukacs, N. W. et al., *J. Immunol.* 1997, 158, 4398). Consistent with this, MCP-1−/−mice displayed a reduced response to challenge with *Schistosoma mansoni* egg (Lu, B. et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerulamephritis resulted in a marked decrease in glomerular crescent formation and deposition of type I collagen (Lloyd, C. M. et al., *J. Exp. Med.* 1997, 185, 1371). In addition, MCP-1−/−mice with induced nephrotoxic serum nephritis showed significantly less tubular damage than their MCP-1+/+counterparts (Tesch, G. H. et al., *J. Clin. Invest.* 1999, 103, 73).

Several studies have demonstrated the potential therapeutic value of antagonism of the MCP-1/CCR2 interaction in treating systemic lupus erythematosus. CCR2−/−mice exhibited prolonged survival and reduced renal disease relative to their WT counterparts in a murine model of systemic lupus erythematosus (Perez de Lema, G. et al. *J. Am. Soc. Neph.* 2005, 16, 3592). These data are consistent with the disease-modifying activity found in recent studies on genetic deletion of MCP-1 (Shimizu, S. et al. *Rheumatology (Oxford)* 2004, 43, 1121; Tesch, G. H. et al., *J. Exp. Med.* 1999, 190, 1813) or administration of a peptide antagonist of CCR2 (Hasegawa, H. et al. *Arthritis & Rheumatism* 2003, 48, 2555) in rodent models of lupus.

A remarkable 30-fold increase in $CCR2^+$ lamina propria lymphocytes was observed in the small bowels from Crohn's patients relative to non-diseased ileum (Connor, S. J. et al., *Gut* 2004, 53, 1287). Also of note, there was an expansion in the subset of circulating $CCR2^+/CD14^+/CD56^+$ monocytes in patients with active Crohn's disease relative to controls. Several rodent studies have demonstrated the potential therapeutic value of antagonism of the MCP-1/CCR2 interaction in treating Crohn's disease/colitis. CCR-2−/−mice were protected from the effects of dextran sodium sulfate-induced colitis (Andres, P. G. et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (Tokuyama, H. et al., *Int. Immunol.* 2005, 17, 1023). Finally, MCP-1−/−mice showed substantially reduced colonic damage (both macroscopic and histological) in a hapten-induced model of colitis (Khan, W. I. et al., *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (Reinecker, H. C. et al., *Gastroenterology* 1995, 108, 40, and Grimm, M. C. et al., *J. Leukoc. Biol.* 1996, 59, 804).

One study described the association of promoter polymorphism in the MCP-1 gene with scleroderma (systemic sclerosis) (Karrer, S. et al., *J. Invest. Dermatol.* 2005, 124, 92). In related models of tissue fibrosis, inhibition of CCR2/MCP-1 axis reduced fibrosis in skin (Yamamoto, T. et al., *J. Invest. Dermatol.* 2003, 121, 510; Ferreira, A. M. et al., *J. Invest. Dermatol.* 2006, 126, 1900), lung (Okuma, T. et al., *J. Pathol.* 2004, 204, 594; Gharaee-Kermani, M. et al., *Cytokine* 2003, 24, 266), kidney (Kitagawa, K. et al., *Am. J. Pathol.* 2004, 165, 237; Wada, T. et al., *J. Am. Soc. Nephrol.* 2004, 15, 940), heart (Hayashidani, S. et al., *Circulation* 2003, 108, 2134), and liver (Tsuruta, S. et al., *Int. J. Mol. Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Jones, M. L. et al., *J. Immunol.* 1992, 149, 2147).

Several studies have shown the potential therapeutic value of antagonism of the MCP-1/CCR2 interaction in treating cancer (reviewed in: Craig, M. J. et al., *Cancer Metastasis Rev.* 2006, 25, 611; Conti, I., *Seminars in Cancer Biology* 2004, 14, 149; Giles, R., *Curr. Cancer Drug Targets* 2006, 6, 659). When immunodeficient mice bearing human breast carcinoma cells were treated with an anti-MCP-1 antibody, inhibition of lung micrometastases and increases in survival were observed (Salcedo, R. et al., *Blood* 2000, 96, 34-40). Using human clinical tumor specimens, CCR2 expression was associated with prostrate cancer progression (Lu, Y. et al., *J. Cell. Biochem.* 2007, 101, 676). In vitro, MCP-1 expression has been shown to mediate prostrate cancer cell growth and invasion (Lu, Y. et al., *Prostate* 2006, 66, 1311); furthermore, MCP-1 expressed by prostate cancer cells induced human bone marrow progenitors for bone resorption (Lu, Y. et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (Cipollone, F. et al., *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Roque, M. et al., *Arterioscler. Thromb. Vasc. Biol.* 2002, 22, 554; Schober, A. et al., *Circ. Res.* 2004, 95, 1125; Kim, W. J. et al., *Biochem Biophys. Res. Commun.* 2003, 310, 936). In mice, transfection of a dominant negative inhibitor of MCP-1 in the skeletal muscle (Egashira, K. et al., *Circ. Res.* 2002, 90, 1167) also reduced intimal hyperplasia after arterial injury. Blockade of CCR2 using a neutralizing antibody reduced neointimal hyperplasia after stenting in primates (Horvath, C. et al., *Circ. Res.* 2002, 90, 488).

Two reports describe the overexpression of MCP-1 rats with induced brain trauma (King, J. S. et al., *J. Neuroimmunol.* 1994, 56, 127, and Berman, J. W. et al., *J. Immunol.* 1996, 156, 3017). In addition, studies have shown that both CCR2−/−(Dimitrijevic, O. B. et al., *Stroke* 2007, 38, 1345) and MCP-1−/−mice (Hughes, P. M. et al., *J. Cereb. Blood Flow Metab.* 2002, 22, 308) are partially protected from ischemia/reperfusion injury.

It is known that monocytes/macrophages play an important role in the development of neuropathic pain (Liu, T. et al., *Pain* 2000, 86, 25). Consistent with this notion, a potential role for CCR2 in the treatment of both inflammatory and neuropathic pain has been described recently. CCR2−/−mice showed altered responses to inflammatory pain relative to their WT counterparts, including reduced pain behavior after intraplantar formalin injection and slightly reduced mechanical allodynia after intraplantar CFA injection (Abbadie, C. et al., *Proc. Natl. Acad. Sci., USA* 2003, 100, 7947). In addition, CCR2−/−mice did not display significant mechanical allodynia after sciatic nerve injury. Likewise, a small molecule CCR2 antagonist reduced mechanical allodynia to ~80% of pre-injury levels after oral administration (Abbadie, C. et al., WO 2004/110376).

One study described the critical role of MCP-1 in ischemic cardiomyopathy (Frangogiannis, N. G. et al., *Circulation* 2007, 115, 584). Another study described the attenuation of experimental heart failure following inhibition of MCP-1 (Hayashidani, S. et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Russell, M. E. et al., *Proc. Natl. Acad. Sci. USA* 1993, 90, 6086). The overexpression of MCP-1 has been noted in the lung endothelial cells of patients with idiopathic pulmonary fibrosis (Antoniades, H. N. et al., *Proc. Natl. Acad. Sci. USA* 1992, 89, 5371). Similarly, the overexpression of MCP-1 has been noted in the skin from patients with psoriasis (Deleuran, M. et al., *J. Dermatol. Sci.* 1996, 13, 228, and Gillitzer, R. et al., *J. Invest. Dermatol.* 1993, 101, 127); correlative findings with predominance of CCR2+ cells have also been reported (Vestergaard, C. et al., *Acta Derm. Venerol.* 2004, 84, 353). Finally, a recent report has shown that MCP-1 is overexpressed in the brains and cerebrospinal fluid of patients with HIV-1-associated dementia (Garzino-Demo, A., WO 99/46991).

In addition, CCR2 polymorphism has been shown to be associated with sarcoidosis at least in one subset of patients (Spagnolo, P. et al., *Am. J. Respir. Crit. Care Med.* 2003, 168, 1162).

It should also be noted that CCR-2 has been implicated as a co-receptor for some strains of HIV (Doranz, B. J. et al., *Cell* 1996, 85, 1149). It has also been determined that the use of CCR-2 as an HIV co-receptor can be correlated with disease progression (Connor, R. I. et al., *J. Exp. Med.* 1997, 185, 621). This finding is consistent with the recent finding that the presence of a CCR-2 mutant, CCR2-64I, is positively correlated with delayed onset of HIV in the human population (Smith, M. W. et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng. J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 or CCR-2 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclohexenyl derivatives for use in therapy.

The present invention provides the use of novel cyclohexenyl derivatives for the manufacture of a medicament for the treatment of inflammatory diseases.

These and other features of the invention, which will become apparent during the following detailed description, have been achieved by the inventors' discovery that compounds of formula (I):

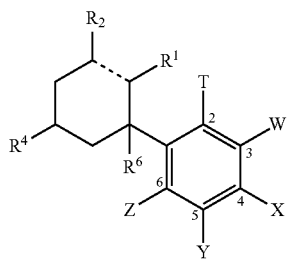

(I)

or stereoisomers or prodrugs or pharmaceutically acceptable salts thereof, wherein T, W, X, Y, Z, $R^1$, $R^2$, $R^4$ and $R^6$, are defined below, are effective modulators of MCP-1 and chemokine activity.

DETAILED DESCRIPTION OF THE PRESENT INVENTION

In one embodiment, the present invention provides novel compounds of formula (I):

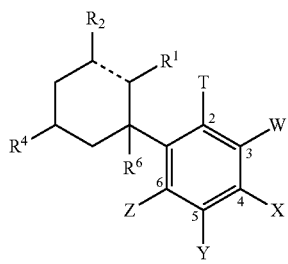

(I)

or a stereoisomer or a pharmaceutically acceptable salt thereof, wherein:
the dotted line represents either a single or a double bond;
$R^1$ is selected from —COOH or —C(=O)NHSO$_2$R$^{12}$;
$R^2$ is H or $C_{1-6}$ alkyl;
$R^4$ is H, $C_{1-4}$ alkyl, $C_{1-4}$ alkoxy, or aryl wherein the $C_{1-4}$ alkyl, $C_{1-4}$ alkoxy and aryl may be optionally substituted with one or more $R^{4a}$'s;
$R^{4a}$ is independently —OH, $C_{1-4}$ alkoxy, —NHC(=O) $C_{1-6}$ alkyl, aryl, or aryloxy;
$R^6$ is selected from H, —OH or $C_{1-4}$ alkyl;
$R^{12}$ is $C_{1-6}$ alkyl, haloC$_{1-6}$ alkyl or aryl;

T is H, $C_{1-4}$ alkyl, haloC$_{1-4}$ alkyl, $C_{1-4}$ alkoxy, or halo;
W is H, $C_{1-4}$ alkyl, haloC$_{1-4}$ alkyl, halo or aryl;
X is H, $C_{1-4}$ alkyl, $C_{1-4}$ alkoxy, or halo;
Y is H, $C_{1-4}$ alkyl, haloC$_{1-4}$ alkyl, $C_{1-4}$ alkoxy, halo or aryl;
Z is selected from H, $C_1$, $C_{1-2}$ alkyl and $C_{1-2}$ alkoxy;
or alternatively any two adjacent T, W, X, Y and Z can be taken together to form a fused cycloalkyl, aryl, heteroaryl, heterocyclyl ring, which may be optionally substitute with one or more $R^{4a}$'s;
provided that:
(1) $R^2$, $R^4$, T, W, X, Y and Z are not all H;
(2) X is not propyl or t-butyl when $R^2$, $R^{11}$, T, W, X, Y and Z are H and $R^4$ and $R^6$ are methyl;
(3) $R^4$ is not methyl or phenyl, when $R^2$, T, Y and Z are H, $R^6$ is methyl, $R^{11}$ is methyl or ethyl, and X and W are both chloro;
(4) W and Y are not both aryl; and
(5) the compound is not:

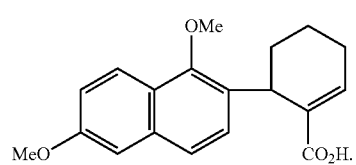

In another embodiment, compounds of the present invention, or a stereoisomer or pharmaceutically acceptable salt from thereof, are those in which the compound is a compound of formula (Ia):

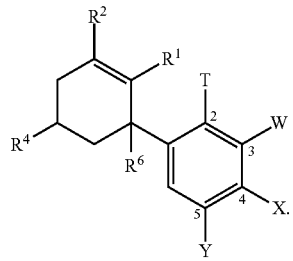

(Ia)

In still yet another embodiment, compounds of the present invention, or a stereoisomer or pharmaceutically acceptable salt from thereof, are those in which:
the dotted line represents a double bond;
$R^1$ is selected from —COOH or —C(=O)NHSO$_2$R$^{12}$;
$R^2$ is H or $C_{1-2}$ alkyl;
$R^4$ is H, $C_{1-2}$ alkyl, $C_{1-2}$ alkoxy, or aryl wherein the $C_{1-2}$ alkyl, $C_{1-2}$ alkoxy and aryl may be optionally substituted with one or more $R^{4a}$'s;
$R^{4a}$ is independently —OH, $C_{1-4}$ alkoxy, —NHC(=O) $C_{1-6}$ alkyl, aryl, or aryloxy;
$R^6$ is selected from H, —OH or $C_{1-2}$ alkyl;
$R^{12}$ is $C_{1-2}$ alkyl, haloC$_{1-6}$ alkyl or phenyl;
T is H, $C_{1-2}$ alkyl, haloC$_{1-2}$ alkyl, or $C_{1-2}$ alkoxy;
W is H, $C_{1-2}$ alkyl, haloC$_{1-2}$ alkyl, halo or aryl;
X is H, $C_{1-2}$ alkyl, $C_{1-2}$ alkoxy, or halo;
Y is H, $C_{1-2}$ alkyl, haloC$_{1-2}$ alkyl, halo or aryl;
Z is H;
or alternatively any two T, W, X, and Y can be taken together to form a fused cycloalkyl, aryl, heteroaryl, heterocyclyl ring, which may be optionally substitute with one or more $R^{4a}$'s.

In one embodiment, compounds of the present invention, or a stereoisomer or pharmaceutically acceptable salt from thereof, are those in which:
the dotted line represents a double bond;
$R^1$ is selected from —COOH or —C(=O)NHSO$_2$R$^{12}$;
$R^2$ is H or C$_{1-2}$ alkyl;
$R^4$ is H or C$_{1-2}$ alkyl, wherein the C$_{1-2}$ alkyl may be optionally substituted with one or more R$^{4a}$s;
$R^{4a}$ is independently —OH, C$_{1-4}$ alkoxy, aryl, —NHC(=O)C$_{1-6}$ alkyl or aryloxy;
$R^6$ is selected from H or C$_{1-2}$ alkyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-2}$ alkyl, C$_{1-2}$ alkoxy, or halo;
Y is H, C$_{1-2}$ alkyl, haloC$_{1-2}$ alkyl, halo or aryl;
Z is H;
or alternatively any two T, W, X, and Y can be taken together to form a fused cycloalkyl, aryl, heteroaryl, heterocyclyl ring, which may be optionally substitute with one or more R$^{4a}$s.

In another embodiment, compounds of the present invention, or a stereoisomer or pharmaceutically acceptable salt from thereof, are those in which:
the dotted line represents a double bond;
$R^1$ is selected from —COOH or —C(=O)NHSO$_2$R$^{12}$;
$R^2$ is H or C$_{1-2}$ alkyl;
$R^4$ is H or C$_{1-2}$ alkyl;
$R^6$ is C$_{1-2}$ alkyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-2}$ alkyl, C$_{1-2}$ alkoxy, or halo;
Y is H, C$_{1-2}$ alkyl, haloC$_{1-2}$ alkyl, halo or aryl;
Z is H;
or alternatively any two T, W, X, and Y can be taken together to form a fused cycloalkyl, aryl, heteroaryl, heterocyclyl ring.

In yet another embodiment, compounds of the present invention, or a stereoisomer or pharmaceutically acceptable salt from thereof, are those in which:
the dotted line represents a double bond;
$R^1$ is selected from —COOH or —C(=O)NHSO$_2$R$^{12}$;
$R^2$ is H or methyl;
$R^4$ is H or methyl;
$R^6$ is methyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-4}$ alkyl, C$_{1-4}$ alkoxy, or halo;
Y is H, C$_{1-2}$ alkyl, haloC$_{1-4}$ alkyl, halo or aryl;
Z is H;
or alternatively any two T, W, X, and Y can be taken together to form a fused cycloalkyl, aryl, heteroaryl, heterocyclyl ring.

In still yet another embodiment, compounds of the present invention, or a stereoisomer or pharmaceutically acceptable salt from thereof, are those in which:
the dotted line represents a double bond;
$R^1$ is —COOH;
$R^2$ is H or methyl;
$R^4$ is H or methyl;
$R^6$ is methyl;
T is H, methyl, —CF$_3$, or methoxy;
W is H, methyl, —CF$_3$, Cl, F or phenyl;
X is H, C$_{1-2}$ alkyl, or halo;
Y is H, C$_{1-2}$ alkyl, haloC$_{1-4}$ alkyl, or halo;
Z is H;
or alternatively any two T, W, X, and Y can be taken together to form a fused cycloalkyl, aryl, heteroaryl, heterocyclyl ring.

In one embodiment, compounds of the present invention, or a stereoisomer or pharmaceutically acceptable salt from thereof, are those in which:
the dotted line represents a double bond;
$R^1$ is —COOH;
$R^2$ is H or methyl;
$R^4$ is H or methyl;
$R^6$ is methyl;
T is H, methyl, —CF$_3$, or methoxy;
W is H, methyl, —CF$_3$, Cl, F or phenyl;
X is H, methyl, Cl, or F;
Y is H, methyl, CF$_3$, Cl, F;
Z is H;
or alternatively any two T, W, X, and Y can be taken together to form a fused cycloalkyl, aryl, heteroaryl, heterocyclyl ring.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-2 receptor activity comprising administering to a patient in need thereof a therapeutically effective amount of a compound of the present invention.

In another embodiment, the present invention is directed to a method for modulation of MCP-1 activity that is mediated by the CCR-2 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-2, comprising administering to a patient in need thereof a therapeutically effective amount of a compound of the present invention.

In another embodiment, the present invention is directed to a method for modulation of CCR2 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-2 receptor activity comprising administering to a patient in need thereof a therapeutically effective amount of a pharmaceutical composition comprised of a compound of the present invention and one or more active ingredients.

In yet another embodiment, the present invention is directed to a method for modulation of MCP-1 activity that is mediated by the CCR-2 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-2, comprising administering to a patient in need thereof a therapeutically effective amount of a pharmaceutical composition comprised of a compound of present invention and one or more active ingredients.

In another embodiment, the present invention is directed to a method for modulation of CCR-2 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

In another embodiment, the present invention provides a compound of the present invention for use in therapy for treating an inflammatory disease.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of an inflammatory disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of an inflammatory disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat an inflammatory disease.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy* 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

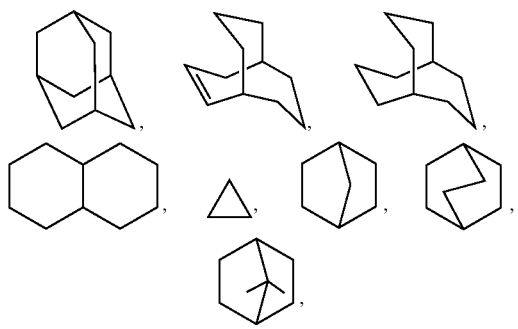

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

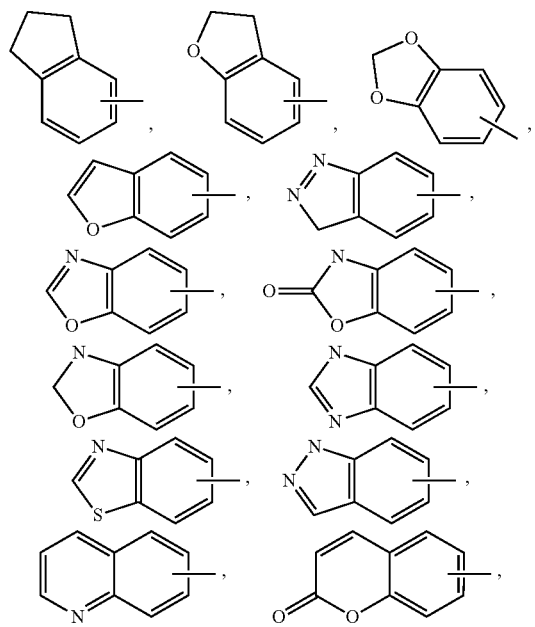

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, piperidonyl, 4-piperidonyl, piperonyl, pyrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., p. 1418 (Mack Publishing Company, Easton, Pa., 1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters, carbamates and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Ch. 31 (Academic Press, 1996);

b) Bundgaard, H., ed., *Design of Prodrugs* (Elsevier, 1985);

c) Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, Ruffolo, Jr., R. R. et al., eds., pp. 173-198 (CRC Press, Inc., 1995); and d) Testa, B. et al., *Hydrolysis in Drug and Prodrug Metabolism* (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition (Wiley and Sons, 1999)).

Some compounds of Formula (I) can be prepared by the routes outlined in Scheme 1, wherein A represents the pendent ring of Formula (I). An appropriate 2-alkoxycarbonyl-cyclohex-2-enone 1-1 (where R is a group such as methyl, ethyl, benzyl or tert-butyl) can be converted to the intermediate β-ketoester 1-2 using methods for conjugate (1,4) addition of an aryl group to an α,β-unsaturated ketoester, for example treatment with an appropriate arylmagnesium halide in the presence of a copper (I) compound such as copper (I) chloride, copper (I) bromide, copper (I) cyanide or copper (I) acetate, in a suitable solvent such as diethyl ether or tetrahydrofuran. Alternatively, enone 1-1 can be treated with a preformed lithium diarylcuprate $A_2CuLi$ in a suitable solvent. Such methods are well-known in the published chemical literature. The resulting β-ketoester (which may exist as the keto form shown in Scheme 1, as the tautomeric enol form, or as a mixture of the two tautomers) can be converted to the β-hydroxyester 1-3 by treatment with a suitable reducing agent, for example sodium borohydride, in a suitable solvent such as methanol. The intermediate 1-3 can be converted to the cyclohexenecarboxylate ester 1-4 (where $R^2$ is hydrogen) by elimination of the hydroxyl group using any of a variety of methods well known in the chemical literature. One example of such methods is conversion of the hydroxyl group of 1-3 to a more active leaving group such as methanesulfonate, trifluoromethanesulfonate or arylsulfonate by treatment with the corresponding sulfonyl chloride or sulfonic anhydride under suitable conditions, followed by treatment with a base such as, for example, DBU. Another example of such methods is treatment of the intermediate 1-3 with an acid and/or acid-solvent combination such as toluenesulfonic acid in toluene, hydrochloric acid in a suitable solvent or trifluoroacetic acid. The intermediate ester 1-4 may be converted to the compound of Formula (I) represented by 1-5 using methods well known in the chemical literature, for example treatment with an aqueous base such as sodium hydroxide or potassium hydroxide, optionally with a suitable cosolvent such as methanol or ethanol, followed by acidification.

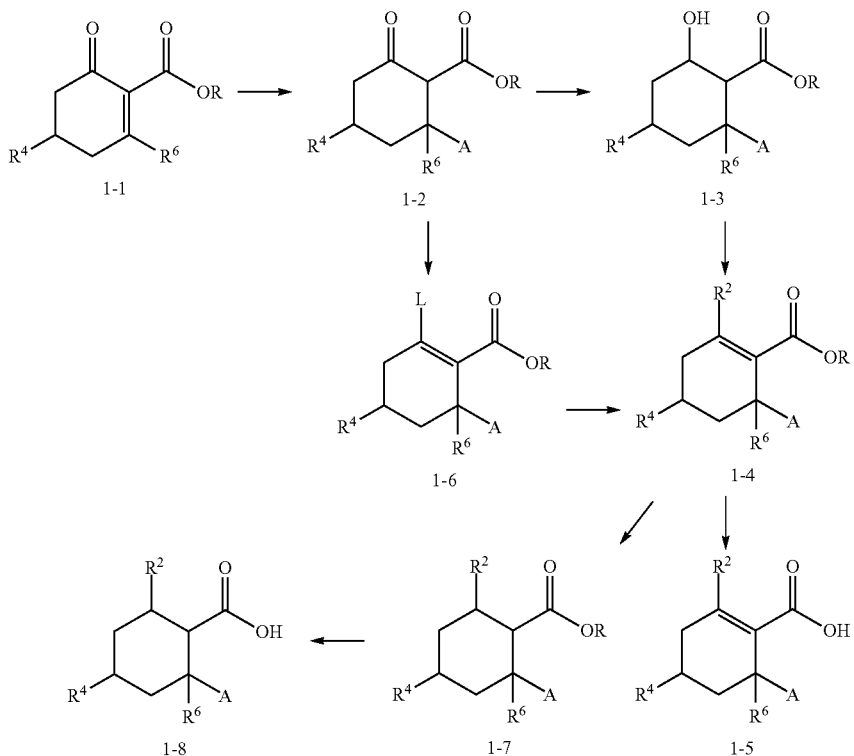

Scheme 1

Intermediates 1-3 can also be converted directly to the compounds of Formula (I) represented by 1-5 by treatment with a base such as sodium hydroxide or potassium hydroxide in a suitable solvent such as water, methanol or ethanol, or a mixture of water and methanol or ethanol, under suitable conditions, followed by acidification.

Intermediates 1-2 can also be converted to intermediates 1-4 wherein $R^2$ is alkyl using procedures well known in the chemical literature. 1-2 can be converted into 1-6 wherein L is a group suitable for replacement with an alkyl moiety. For example, treatment of 1-2 with a base such as sodium hydride in a suitable solvent such as diethyl ether or tetrahydrofuran, followed by treatment of the resulting anion with a chlorophosphate such as dimethyl chlorophosphate or diethyl chlorophosphate (as reported by Sum et al., *Can. J. Chem.* 1979, 57, 1431), can provide the intermediates 1-6 where L is a dialkylphosphoryloxy group. Treatment of these intermediates with a lithium dialkylcuprate can provide the intermediates 1-4 (where $R^2$ is an alkyl group), which can then be converted to the compounds of Formula I represented by 1-5, for example by hydrolysis with aqueous sodium or potassium hydroxide as described above.

Intermediates 1-4 can be converted to intermediates 1-7 by reduction of the carbon-carbon double bond using methods well known in the chemical literature, for example by hydrogenation in the presence of a catalyst such as palladium or platinum on powdered carbon. The resulting cyclohexanecarboxylic acid esters 1-7 can be converted to the compounds of Formula I represented by 1-8, for example by hydrolysis with aqueous sodium or potassium hydroxide as described above.

Intermediates represented by structure 1-1 of Scheme 1 can also be converted to compounds of Formula I where $R^6$ is hydroxy and A is the pendent ring of Formula I, as shown in Scheme 2. Compounds 2-1 (which are the same as compounds 1-1 in Scheme 1, but with $R^6$ changed to $R^2$) can be treated with an appropriate arylmagnesium halide or aryllithium reagent in a suitable solvent such as diethyl ether or tetrahydrofuran to provide intermediates 2-2. Hydrolysis of the ester as described for Scheme 1 can provide compounds of Formula I represented by 2-3 (where the dotted line represents a double bond). Alternatively, either the intermediates 2-2 or the products 2-3 (where the dotted line represents a double bond) can be hydrogenated as described above, followed by hydrolysis in the case of 2-2 as the starting material, to provide compounds of Formula I represented by 2-3 (where the dotted line represents a single bond).

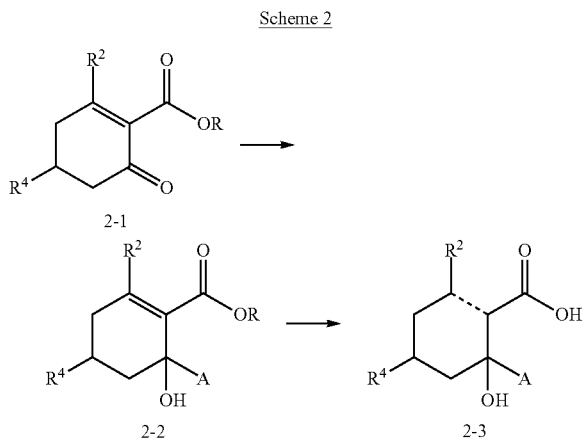

Scheme 2

Intermediates 1-1 and 2-1 can be prepared using methods known in the chemical literature, for example as shown in Scheme 3. Following the procedure of Belmont, D. T. et al., *J. Org. Chem.* 1985, 50, 4102, a δ-ketoacid 3-2 can be converted to the dihydropyranones 3-3 by treatment with a reagent such as thionyl chloride. (One example of the preparation of ketoacids 3-2 is the reaction of the symmetrical anhydrides 3-1 with N,O-dimethylhydroxylamine, followed by reaction of the resulting intermediates with an alkyllithium reagent $R^6Li$ in a suitable solvent such as diethyl ether or tetrahydrofuran.) The intermediates 3-3 can then be converted to the alkoxycarbonylcyclohexenones 3-4 (equivalent or similar to 1-1 and 2-1 where $R^6$ is not H) by treatment with the anion of an alkyl acetate, again following the procedure of Belmont, D. T. et al., *J. Org. Chem.* 1985, 50, 4102.

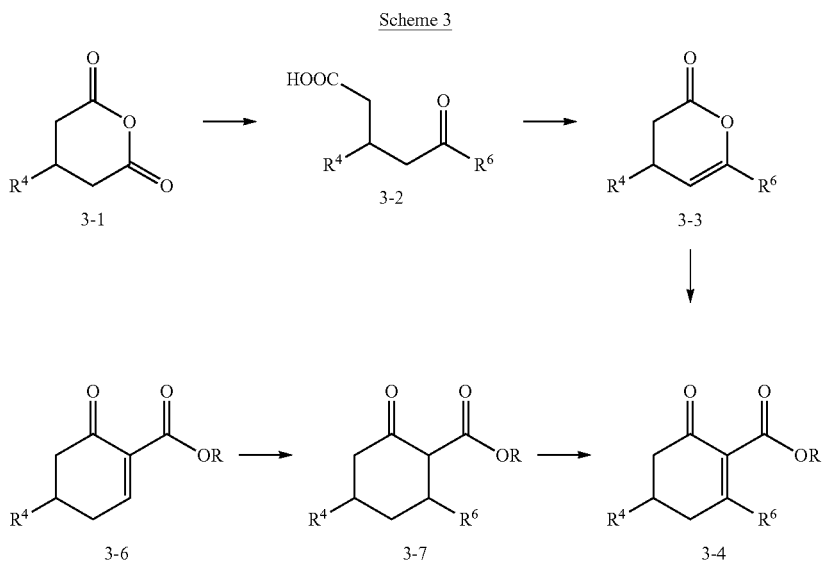

Scheme 3

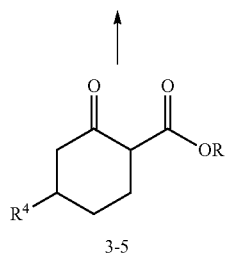

3-5

Alternatively, an alkoxycarbonylcyclohexanone 3-5 can be converted to the intermediates 3-6 (equivalent to 1-1 with $R^6$=H, or to 2-1 with $R^2$=H) by treatment of the anion (formed by treatment with a base such as pyridine or sodium hydride in a suitable solvent such as dichloromethane or tetrahydrofuran) with phenylselenium chloride, followed by oxidative elimination of the intermediate phenylselenium derivative, for example with hydrogen peroxide. The intermediates 3-6 can additionally be treated with an alkylmagnesium halide such as $R^6$MgCl or $R^6$MgBr in the presence of a copper (I) salt such as copper (I) chloride, copper (I) bromide or copper (I) cyanide, or with a preformed lithium dialkylcuprate $R^6_2$CuLi, in a suitable solvent such as diethyl ether or tetrahydrofuran, to provide intermediates 3-7. These can then be converted to intermediates 3-4 by conversion to the phenylselenium derivative and oxidative elimination as described above.

Some compounds of Formula (I) can be prepared by the routes outlined in Scheme 4, wherein A represents the pendent ring of Formula (I). Cyclohexanones of structure 4-1 (where $R^6$ is alkyl) can be converted to the enol trifluoromethane-sulfonates 4-2 by treatment with a base such as sodium bis(trimethylsilyl)amide in a suitable solvent such as tetrahydrofuran, followed by treatment of the intermediate anions with a reagent such as N-(5-chloropyridin-2-yl)-trifluoromethanesulfonimide (also known as Comin's reagent). The intermediates 4-2 can then be converted to the alkoxycarbonyl intermediates 4-3 (where R is, for example, methyl or ethyl) by treatment with carbon monoxide and a suitable alcohol such as methanol or ethanol, in the presence of a suitable catalyst, such as palladium (II) acetate, a suitable ligand such as bis-(diphenylphosphino)ferrocene, and a suitable base such as triethylamine or diisopropylethylamine, in a suitable solvent such as N,N-dimethylformamide (see, for example, Cacchi, S. et al., *Tetrahedron Lett.* 1985, 26, 1109). The resulting intermediates can then be converted to compounds of Formula (I), represented by 4-3 where R is H, by hydrolysis as described for Scheme 1. Alternatively, carboxylation of intermediates 4-2 can directly provide compounds of formula (I) represented by 4-3 where R is H, by substitution of water for the alcohol.

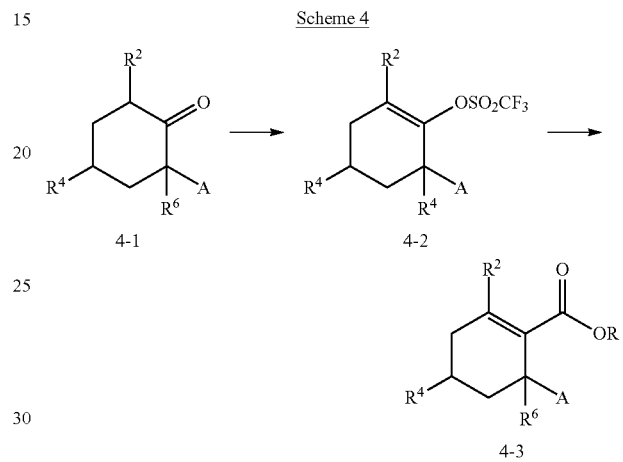

Scheme 4

Intermediates of structure 4-1 in Scheme 4 can be prepared by procedures shown in Scheme 5. An epoxide of structure 5-1 can be reacted with an aryllithium reagent A-Li in a suitable solvent such as tetrahydrofuran, optionally with a Lewis acid additive such as boron trifluoride etherate, to provide the alcohols 5-2 (see, for example, Chini et al., *Tetrahedron Lett.* 1989, 30, 6563). This method is particularly suitable for cases where $R^4$=alkoxy or benzyloxy. The alcohols 5-2 can be oxidized to the ketones 5-3 (equivalent to intermediates 4-1 where $R^2$ and $R^6$ are both H) using any of a variety of procedures well-known in the chemical literature, for example using dimethylsulfoxide, an activating agent such as oxalyl chloride and a base such as triethylamine (the Swern oxidation), or using a transition metal oxidant such as pyridinium chlorochromate. The ketones 5-3 may also be converted to the thermodynamically more stable anion and alkylated with a suitable alkylating agent (for example as reported by Paquette et al., *J. Org. Chem.* 1989, 54, 5044) to provide intermediates 5-4 where $R^6$ is alkyl (equivalent to intermediates 4-1 where $R^2$ is H). The intermediates 5-4 where $R^6$ is alkyl may also be further alkylated by conversion to the anion and treatment with a suitable alkylating agent to provide intermediates 5-5 (equivalent to intermediates 4-1).

Scheme 5

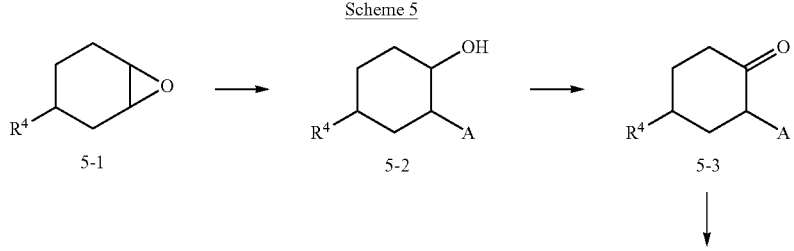

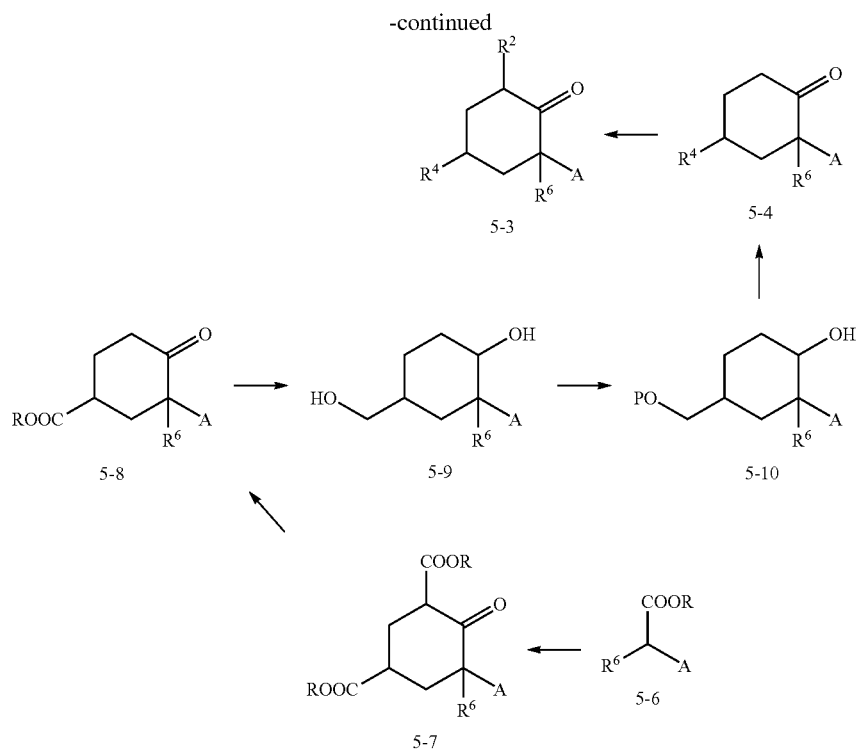

Intermediates of structure 4-1 in Scheme 4 can also be prepared by alternative procedures shown in Scheme 5. Arylacetic esters 5-6 where $R^6$ is H may be prepared from the corresponding aryl aldehyde A-CHO using methods reported in the chemical literature, for example as reported by Boes et al., *Helv. Chim. Acta* 1998, 81, 525, or from the corresponding aryl bromide A-Br, for example as reported by Heck et al., *Tetrahedron Lett.* 1981, 22, 5027. Arylacetic esters 5-6 where $R^6$ is alkyl may be prepared from arylacetic esters 5-6 where $R^6$ is H by formation of the anion with a suitable base and alkylation with a suitable alkylating agent. Intermediates 5-6 may be converted to intermediates 5-7 by treatment with a suitable base and an alkyl acrylate ester, as reported by Posner et al., *J. Org. Chem.* 1989, 54, 3514. Decarboxylation of intermediates 5-7, for example by heating with sodium chloride and water in dimethylsulfoxide, can provide intermediates 5-8. Reduction of intermediates 5-8, for example with sodium borohydride in a suitable solvent, can provide the diols 5-9. Using any of a variety of methods well known in the chemical literature, selective protection of the primary hydroxyl group with a suitable protecting group P, such as tert-butyldiphenylsilyl, followed by oxidation of the secondary hydroxyl group of 5-10, can provide intermediates 5-4 (where $R^4$ is $CH_2OP$). This substituent $R^4$ can be used to prepare other substituents $R^4$ as described below.

In the cases where this procedure commences with intermediates 5-6 having $R^6$=H, the corresponding intermediates 5-8 can be converted to the anion and alkylated as described previously, to provide intermediates 5-8 where $R^6$ is alkyl.

Compounds of Formula (I) where $R^1$ is $C(=O)NHSO_2R$ can be prepared from compounds of Formula (I) where $R^1$ is COOH, for example by treatment with a sulfonamide $RSO_2NH_2$ in the presence of a coupling reagent such as ethyl N,N-dimethylaminoethylcarbodiimide and a base such as 4-(N,N-dimethylamino)pyridine, in a suitable solvent such as dichloromethane or N,N-dimethylformamide. Such reactions are well known in the chemical literature.

Compounds of Formula (I) where $R^1$ is 5-tetrazolyl can be prepared from compounds of formula (I) where $R^1$ is COOH using methods known in the literature, for example via an amide as reported by Duncia et al., *J. Org. Chem.* 1991, 56, 2395.

Various substituents $R^4$ in compounds of Formula (I) can be prepared from other substituents $R^4$ using standard methods well known in the chemical literature. Such transformations may be done at the stage of any suitable intermediate in the preparation of compounds of Formula (I). Some examples are given below, which are not meant to be limiting but only illustrate some of the possibilities for the preparation of various $R^4$ substituents.

A substituent $R^4$=$CH_2OP$, where P is a suitable protecting group (as described in the discussion of Scheme 5) can be converted to $R^4$=$CH_2OH$ by deprotected using standard methods. A substituent $R^4$=$CH_2OH$ can be converted to $R^4$=$CH_2$—O-alkyl by reaction under suitable conditions, for example by treatment with iodomethane in the presence of silver oxide, or by treatment with isobutylene in the presence of an acid catalyst. A substituent $R^4$=$CH_2OH$ can be converted to $R^4$=$CH_2NHC(=O)$alkyl, for example by reaction with hydrazoic acid in the presence of triphenylphosphine and a dialkyl azodicarboxylate (commonly called the Mitsunobu displacement reaction), reduction of the resulting compound with $R^4$=$CH_2N_3$, for example with triphenylphosphine and water (commonly called the Staudinger reduction), and acylation of the resulting compound with $R^4$=$CH_2NH_2$, for example with an acyl halide or an acyl anhydride in the presence of a suitable base.

In many cases described above, mixtures of diastereomeric compounds may be obtained from some reactions. These diastereomers may be separated using standard chromatographic methods. In some cases, one diastereomer may be converted into a mixture of two diastereomers, allowing isolation of the second diastereomer by chromatographic separation. For example, in the case of intermediates 5-8 in Scheme 5, where $R^6$ is alkyl, one diastereomer may be partially converted into another by equilibration catalyzed by a base such as sodium methoxide in a suitable solvent such as methanol.

The compounds of Formula (I) contain at least one chiral center, and thus may exist as racemic mixtures or non-racemic mixtures of enantiomers. The two enantiomers may be separated using methods well known in the chemical literature, for example by selective crystallization of a carboxylate salt formed with an optically-active base followed by acidification, or by chromatography on a chiral stationary phase.

Other features of the invention will become apparent in the course of the following descriptions of exemplary embodiments that are given for illustration of the invention and are not intended to be limiting thereof.

EXAMPLES

Abbreviations used in the Examples are defined as "2×" for twice, "° C." for degrees Celsius, "g" for gram or grams, "mmol" for millimolar, "mL" for milliliter or milliliters, "μL" for microliter or microliters, "M" for molar, "min" for minute or minutes, "mg" for milligram or milligrams, "h" for hour or hours, "LC" for liquid chromatography, "HPLC" for high performance liquid chromatography, "MS" for mass spectroscopy, "rt" or "RT" for room temperature, "THF" for tetrahydrofuran, "DMSO" for dimethylsulfoxide, "Et$_2$O" for diethyl ether, "DBU" for 1,8-diazabicyclo[5.4.0]undec-7-ene, "EDC" for N-(3-dimethylaminopropyl)-N'-ethylcarbodiimide hydrochloride, "dppf" for 1,1'-bis(diphenylphosphino)ferrocene, "dmap" for 4-(N,N-dimethylamino)pyridine, "sat." for saturated, "N" for normal, and "HCl" for hydrochloric acid. "D", "L", "R" and "S" are stereochemical designations familiar to those skilled in the art. Chemical names were derived using ChemDraw Ultra Version 9.0.5 (CambridgeSoft). When this program failed to provide a name for the exact structure in question, an appropriate name was assigned using the same methodology utilized by the program.

Example 1-01

Preparation of racemic 6-(3,4-dichlorophenyl)-6-methylcyclohex-1-enecarboxylic acid Step 1. A suspension of copper (I) chloride (164 mg) in THF (4 mL) was stirred at 0° C. and treated with 3,4-dichlorophenylmagnesium bromide (0.5 M in THF, 3.3 mL). The mixture was stirred for 5 min, then was treated with a solution of methyl 2-methyl-6-oxocyclohex-1-enecarboxylic acid (prepared according to the procedure of Belmont, D. T. et al., *J. Org. Chem.* 1985, 50, 4102; 140 mg) in THF. The mixture was allowed to warm to rt over 30 min, then was cooled to 0° C. and treated with a 9:1 solution of saturated ammonium chloride-concentrated ammonium hydroxide. The mixture was extracted three times with ethyl acetate and the combined organic layers were washed with saturated aqueous ammonium chloride, dried over sodium sulfate and then concentrated under vacuum. The resulting residue was filtered through silica gel to provide methyl 2-(3,4-dichlorophenyl)-6-methylcyclohexanecarboxylate (153 mg). Mass spectrum m/z 316.44 (M+H$^+$).

Step 2. A solution of methyl 2-(3,4-dichlorophenyl)-6-methylcylcohexanecarboxylate (153 mg) in methanol (5 mL) was cooled to 0° C. and treated with sodium borohydride (55 mg). The mixture was allowed to warm to rt and stirred for 2 h, then was partitioned between ethyl acetate and water. The organic phase was washed with 5% aqueous HCl, dried over magnesium sulfate and concentrated under vacuum. The resulting crude product was purified by silica gel chromatography, eluting with 3:1 hexanes-ethyl acetate, to provide methyl 2-(3,4-dichlorophenyl)-6-hydroxy-2-methylcyclohexane-carboxylate (152 mg). Mass spectrum m/z 318.24 (M+H$^+$).

Step 3. A solution of methyl 2-(3,4-dichlorophenyl)-6-hydroxy-2-methylcyclohaxanecarboxylate (152 mg) in dichloromethane (5 mL) was stirred at 0° C. and treated with methanesulfonic anhydride (84 mg) and 2,6-lutidine (113 μL). The mixture was warmed to rt and stirred overnight, then was concentrated under vacuum. The resulting residue was dissolved in ethyl acetate, washed sequentially with water, saturated aqueous sodium bicarbonate and saturated sodium chloride, dried over magnesium sulfate and concentrated under vacuum to yield methyl 2-(3,4-dichloro-phenyl)-2-methyl-6-(methanesulfonyloxy)cyclohexane-carboxylate (185 mg). Mass spectrum m/z 417.04 (M+H$^+$).

Step 4. A solution of methyl 2-(3,4-dichlorophenyl)-2-methyl-6-(methylsulfonyloxy)cyclohexanecarboxylate (185 mg) in benzene (5 mL) was stirred at rt and treated with DBU (131 μL). The mixture was heated to 60° C. and stirred for 36 h. The cooled mixture was treated with water and extracted with ethyl acetate. The organic layer was washed with saturated aqueous sodium bicarbonate and saturated aqueous sodium chloride, dried over magnesium sulfate and concentrated under vacuum to provide methyl 6-(3,4-dichlorophenyl)-6-methylcyclohex-1-enecarboxylate (142 mg). Mass spectrum m/z 321.12 (M+Na$^+$).

Step 5. A solution of methyl 6-(3,4-dichlorophenyl)-6-methylcyclohex-1-enecarboxylate (142 mg) in ethanol (5 mL) was treated with aqueous potassium hydroxide (3 M, 1.6 mL) and the mixture was heated at 60° C. for 2 h. After this time, the mixture was cooled to rt, acidified with 1 M aqueous HCl and then extracted three times with ethyl acetate. The combined organic layers were washed with saturated sodium chloride, dried over sodium sulfate and concentrated under vacuum. The resulting residue was purified by preparative HPLC to provide Example 1-01 (6.5 mg). Mass spectrum m/z 287.12 (M+H$^+$).

Example 1-02

Preparation of racemic 6-(4-chlorophenyl)-6-methyl-cyclohex-1-enecarboxylic acid Step 1. A suspension of copper acetate (67 mg) in THF (10 mL) was stirred at 0° C. and treated with 4-chlorophenylmagnesium bromide (1.0 M in diethyl ether, 4 mL). The resulting mixture was stirred at rt for 2 h, and then treated with 9:1 saturated aqueous ammonium chloride-concentrated ammonia. The mixture was stirred for 5 min and then extracted with ethyl acetate. The organic layer was washed with saturated aqueous sodium chloride, dried over sodium sulfate and concentrated under vacuum to provide methyl 2-(4-chlorophenyl)-2-methyl-6-oxocyclohexanecarboxylate (173 mg). Mass spectrum m/z 303.12 (M+Na$^+$).

Steps 2-5. Using the procedures of Steps 2-5 of Example 1-01, methyl 2-(4-chlorophenyl)-2-methyl-6-oxocyclohexanecarboxylate was converted into Example 1-02. Mass spectrum m/z 249.08 (M−H$^-$).

Example 1-03

Preparation of (4RS,6RS)-6-(3-phenylphenyl)-4,6-dimethylcyclohex-1-enecarboxylic acid Step 1. A solution of 3-methylglutaric anhydride (5.0 g) and N,O-dimethylhydroxylamine hydrochloride (4.19 g) in dichloromethane (100 mL) was stirred at 0° C. and treated dropwise with pyridine (6.9 mL). The resulting solution was warmed to rt over 45 min and then stirred overnight. After this time, the mixture was concentrated under vacuum, and the resulting residue was taken up in saturated aqueous sodium chloride and 1:1 ether/dichloromethane. The aqueous and organic layers were separated and the aqueous layer was extracted three times with dichloromethane. The combined organic layers were dried over magnesium sulfate and concentrated under vacuum to provide 5-(methoxy(methyl)amino)-3-methyl-5-oxopentanoic acid as a yellow oil (7.27 g). Mass spectrum m/z 188.10 (M−H⁻).

Step 2. A solution of 5-(methoxy(methyl)amino)-3-methyl-5-oxopentanoic acid (10 mmol) in THF (50 mL) and cooled to −78° C. and treated dropwise with methyllithium (1.4 M in diethyl ether, 2 equivalents). The resulting mixture was warmed to rt where it stirred overnight. After this time, the mixture was cooled to 0° C. and then treated with ice cold water. After stirring for 10 min at 0° C., the mixture was acidified with cold 1 M aqueous HCl. The acidified mixture was extracted three times with ethyl acetate, and the combined organic layers were washed with saturated aqueous sodium chloride, dried over magnesium sulfate and concentrated under vacuum to provide 3-methyl-5-oxohexanoic acid (quantitative yield). Mass spectrum m/z 143.22 (M−H⁻).

Step 3. A solution of 3-methyl-5-oxohexanoic acid (2.1 g) in benzene (26 mL) was treated at rt with thionyl chloride (1.26 mL). The mixture was heated to 85° C. where it stirred for 2 days. At the conclusion of this period, the mixture was cooled to rt and concentrated under vacuum to provide 4,6-dimethyl-3,4-dihydropyran-2-one as a dark brown oil, which was used directly in Step 4 without purification. Mass spectrum m/z 127.37 (M+H⁺).

Step 4. A solution of diisopropylamine (1.9 mL) in THF (18 mL) at 0° C. was treated with n-butyllithium (1.6 M in hexane, 8.4 mL). The resulting yellow solution was stirred at 0° C. for 10 min and then cooled to −78° C. Once at the prescribed temperature, methyl acetate (8.4 mL) was added dropwise and the stirring was continued at −78° C. for 30 min. After this time, a solution of crude 4,6-dimethyl-3,4-dihydropyran-2-one (1.5 g) in THF (4 mL) was added rapidly. The resulting mixture was stirred at −78° C. for 1 h and then warmed to rt. Once at the prescribed temperature, saturated aqueous ammonium chloride (37 mL) was added and the aqueous and organic layers were separated. The organic layer was washed with saturated aqueous sodium chloride, dried over sodium sulfate and concentrated under vacuum to provide an inseparable mixture of methyl 2-hydroxy-2,4-dimethyl-6-oxocylohexanecarboxylate and methyl 5-methyl-3,7-dioxooctanoate as an oil. This oil was dissolved in benzene (240 mL) and then with rapid stirring at rt was treated with methanesulfonic acid (3.3 mL). The resulting solution was stirred at rt for 5 min and then treated with saturated aqueous sodium bicarbonate (240 mL). The aqueous and organic layers were separated and the organic layer was washed with saturated sodium chloride, dried over sodium sulfate and concentrated under vacuum to yield a residue. The residue was purified by chromatography on silica gel, eluting with 20% ethyl acetate/hexanes, to provide racemic methyl 2,4-dimethyl-6-oxocyclohex-1-enecarboxylate as an oil (580 mg). Mass spectrum m/z 205.16 (M+Na⁺).

Step 5. A solution of 3-bromobiphenyl (403 µL) in diethyl ether (4 mL) was stirred at −90° C. and treated slowly with n-butyllithium (1.6 M in hexanes, 1.5 mL). The resulting mixture was stirred at −90° C. for 20 min, and then transferred via a cannula to a stirred suspension of copper (I) cyanide (98 mg) in diethyl ether (1 mL) at −78° C. The mixture was stirred for 10 min at −78° C. and then warmed to 0° C. Once at the prescribed temperature, a solution of methyl 2,4-dimethyl-6-oxocyclohex-1-enecarboxylate (100 mg) in diethyl ether (1 mL) was added and the resulting mixture was warmed to rt over 30 min. Once at the prescribed temperature, the mixture was stirred at rt for 3 h. At the conclusion of this period, the mixture was treated with a 9:1 mixture of saturated aqueous ammonium chloride/ammonium hydroxide (10 mL). The resulting mixture was stirred for 10 min and then extracted three times with diethyl ether. The combined organic layers were washed with saturated aqueous ammonium chloride and saturated sodium chloride, dried over sodium sulfate and concentrated under vacuum to yield a residue. The residue was purified by chromatography on silica gel, eluting with 10% ethyl acetate/hexanes, to provide methyl (2RS,4RS)-2-(3-phenylphenyl)-2,4-dimethyl-6-oxocyclohexanecarboxylate (131.5 mg). Mass spectrum m/z 359.34 (M+Na⁺).

Step 6. A solution of methyl (2RS,4RS)-2-(3-phenylphenyl)-2,4-dimethyl-6-oxocyclohexanecarboxylate (131 mg) in methanol (4 mL) at 0° C. was treated with sodium borohydride (44 mg). The resulting mixture was allowed to warm to rt over 30 min. Once at the prescribed temperature, the mixture was stirred for 2 h, and then was concentrated under vacuum. The resulting residue was dissolved in ethyl acetate and washed with saturated aqueous sodium bicarbonate and saturated aqueous sodium chloride, dried over sodium sulfate and concentrated under vacuum to provide methyl (2RS,4RS)-2-(3-phenylphenyl)-6-hydroxy-2,4-dimethylcyclohexanecarboxylate (93 mg) as a mixture of diastereomers. Mass spectrum m/z 361.34 (M+Na⁺).

Step 7. A solution of methyl (2RS,4RS)-2-(3-phenylphenyl)-6-hydroxy-2,4-dimethylcyclohexanecarboxylate (the mixture of diastereomers from Step 6, 93 mg) in methanol (4 mL) was treated with aqueous sodium hydroxide (3 M, 1 mL). The resulting mixture was heated at 50° C. for 24 h. After this time, the mixture was cooled to rt and concentrated under vacuum. The resulting residue was taken up in ethyl acetate and then washed sequentially with 1 M aqueous HCl and saturated aqueous sodium chloride. The organic layer was dried over sodium sulfate and concentrated under vacuum to yield a residue. This residue was purified by preparative HPLC to provide Example 1-03 (5.6 mg). Mass spectrum m/z 305.20 (M−H⁻).

Example 1-04

Preparation of (4RS,6RS)-6-(3-chloro-4-methylphenyl)-4,6-dimethylcyclohex-1-enecarboxylic acid Step 1. Using the procedure of Example 1-01, but substituting 3-chloro-4-methylphenylmagnesium bromide (0.5 M) in place of 3,4-dichlorophenylmagensium bromide, racemic methyl 2,4-dimethyl-6-oxocyclohex-1-enecarboxylate (prepared according to the procedures of Example 1-03, Steps 1 through 4) was converted to methyl (2RS,4RS)-2-(3-chloro-4-methylphenyl)-2,4-dimethyl-6-oxocyclohexanecarboxylate.

Step 2. Using the procedure of Example 1-01, Step 2, methyl (2RS,4RS)-2-(3-chloro-4-methylphenyl)-2,4-dimethyl-6-oxocyclohexanecarboxylate was converted to methyl (2RS,4RS)-2-(3-chloro-4-methylphenyl)-6-hydroxy-2,4-dimethylcyclohexanecarboxylate as a mixture of diastereomers.

Step 3. A solution of methyl (2RS,4RS)-2-(3-chloro-4-methylphenyl)-6-hydroxy-2,4-dimethylcyclohexanecarboxylate (the mixture of diastereomers from Step 2, 210 mg) in methanol (2 mL) was treated with 6 M aqueous potassium hydroxide (2 mL). The resulting mixture was heated to reflux where it stirred for 8 h. After this time, the mixture was cooled to rt and then concentrated under vacuum to yield a residue. The residue was partitioned between dichloromethane and 1 M aqueous HCl. The aqueous and organic layers were separated and the aqueous layer was extracted twice with dichloromethane. The combined organic layers were dried over sodium sulfate and concentrated under vacuum to yield a residue. This residue was purified by column chromatography on silica gel, eluting with 20% ethyl acetate/hexanes, to provide Example 1-04 as a white solid (118 mg). Mass spectrum m/z 301.21 (M+Na$^+$).

Example 1-05

Preparation of (4RS,6RS)-6-(3,4-difluorophenyl)-4,6-dimethylcyclohex-1-enecarboxylic acid Step 1. A suspension of phenylselenium chloride (27.29 g) in dichloromethane (250 mL) was stirred at 0° C. and treated dropwise with pyridine (11.81 g). The resulting mixture was stirred for 30 min, and then treated with a solution of racemic ethyl 4-methyl-2-oxocyclohexanecarboxylate (25 g) in dichloromethane (20 mL) in one portion. The color changed from brown to yellow, and the mixture was stirred at 0° C. for 15 min. After this time, the mixture was washed twice with 1 M aqueous HCl. The organic layer was cooled to 0° C. and then treated with 30% aqueous hydrogen peroxide (10.5 mL). After stirring for 10 min, an additional 30% aqueous hydrogen peroxide (10.5 mL) was added, followed by another an additional 30% aqueous hydrogen peroxide (10.5 mL) after 20 min. The resulting solution was stirred for 15 min and then treated with water (100 mL). The aqueous and organic layers were separated and the aqueous layer was extracted twice more with dichloromethane. The combined organic layers were washed with saturated aqueous sodium bicarbonate, dried over magnesium sulfate and concentrated under vacuum to provide racemic ethyl 4-methyl-6-oxocyclohex-1-enecarboxylate (26 g).

Step 2. A suspension of copper (I) chloride (10.86 g) in THF (200 mL) was stirred at 0° C. and treated dropwise with methyllithium (1.5 M, 73 mL). The resulting solution was stirred for 30 min at 0° C. and then treated dropwise with a solution of racemic 4-methyl-6-oxocyclohex-1-enecarboxylate (10 g) in THF (30 mL). The resulting mixture was stirred at 0° C. for 3 h, and then treated with saturated aqueous ammonium chloride (300 mL). The mixture was extracted three times with ethyl acetate. The combined organic layers were washed with saturated aqueous ammonium chloride (4×200 mL) and saturated aqueous sodium chloride, dried over magnesium sulfate and concentrated under vacuum to yield a residue. The residue was purified by column chromatography on silica gel, eluting with hexanes, to provide ethyl 2,4-dimethyl-6-oxocylclohexanecarboxylate as a colorless oil (8.02 g). The diastereomeric composition of this material was not characterized.

Step 3. Ethyl 2,4-dimethyl-6-oxocyclohexanecarboxylate (from Step 2, 0.5 g) was added dropwise to a stirred suspension of sodium hydride (60% in mineral oil, 0.15 g, washed with hexane) in THF at 0° C. After addition was complete, the mixture was stirred at 0° C. for 10 min and then a solution of phenylselenium chloride (0.58 g) in THF was added dropwise. The resulting mixture was slowly warmed to rt where it stirred overnight. After this time, the mixture was treated with saturated aqueous sodium bicarbonate and extracted three times with ethyl acetate. The combined organic layers were concentrated under vacuum and the resulting residue was dissolved in dichloromethane. This solution was treated with 30% aqueous hydrogen peroxide (3×0.3 mL, added at 10 min intervals) and the mixture was stirred for an additional 30 min. At the conclusion of this period, the mixture was washed with water and concentrated under vacuum to yield a residue. This residue was purified by column chromatography on silica gel, eluting with 10% ethyl acetate/hexanes, to provide racemic ethyl 2,4-dimethyl-6-oxocyclohex-1-enecarboxylate as an oil (200 mg).

Step 4. Using the procedure of Step 1, Example 1-01, but substituting 3,4-difluorophenylmagnesium bromide (0.5 M) in place of 3,4-dichlorophenylmagensium bromide, racemic ethyl 2,4-dimethyl-6-oxocyclohex-1-enecarboxylate was converted to ethyl (2RS,4RS)-2-(3,4-difluorophenyl)-2,4-dimethyl-6-oxocyclohexanecarboxylate.

Step 5. Using the procedure of Step 2, Example 1-01, ethyl (2RS,4RS)-2-(3,4-difluorophenyl)-2,4-dimethyl-6-oxocyclohexane-carboxylate was converted to ethyl (2RS,4RS)-2-(3,4-difluorophenyl)-6-hydroxy-2,4-dimethylcyclohexanecarboxylate as a mixture of diastereomers.

Step 6. A solution of ethyl (2RS,4RS)-2-(3,4-difluorophenyl)-6-hydroxy-2,4-dimethylcyclohexanecarboxylate (the diastereomeric mixture from Step 5, 120 mg) in methanol (2 mL) was treated with a methanolic solution of sodium hydroxide (30%, 0.5 mL). The resulting mixture was heated to reflux where it stirred for 3 h. After this time, the mixture was cooled to rt, and then concentrated under vacuum. The resulting residue was acidified with 1 M aqueous HCl and the acidified mixture was extracted three times with dichloromethane. The combined organic layers were concentrated under vacuum to yield a residue. This residue was purified by column chromatography on silica gel, eluting with 20% ethyl acetate/hexanes, to provide Example 1-05 as an oil (70 mg). Mass spectrum m/z 289.34 (M+Na$^+$).

Example 1-06

Preparation of (4RS,6RS)-6-(3,4-dichlorophenyl)-6-methyl-4-phenylcyclohex-1-enecarboxylic acid Step 1. A solution of 2-phenylglutaric acid (5 g) in acetic anhydride (100 mL) was stirred at 120° C. for 60 h. At the conclusion of this period, the mixture was cooled to rt and concentrated under vacuum to yield a residue. The residue was twice taken up in dichloromethane and the resulting solution was concentrated to yield a residue. This residue was dissolved in dichloromethane (100 mL) and treated with N,O-dimethylhydroxylamine hydrochloride (2.57 g) followed by triethylamine (8 mL). The resulting mixture was stirred at rt for 12 h, and then quenched with 1 M aqueous HCl (200 mL). The resulting mixture was extracted three times with ethyl acetate. The combined organic layers were washed with saturated aqueous sodium chloride, dried over magnesium sulfate and concentrated under vacuum to provide 5-(methoxy(methyl)amino)-5-oxo-3-phenylpentanoic acid (7 g).

Steps 2-4. Following the procedures of Steps 2-4, Example 1-03, 5-(methoxy(methyl)amino)-5-oxo-3-phenyl-pentanoic acid was converted to racemic methyl 2-methyl-6-oxo-4-phenylcyclohex-1-enecarboxylate. Mass spectrum m/z 267 (M+Na$^+$).

Steps 5-9. Following the procedures of Step 1-5, Example 1-01, racemic methyl 2-methyl-6-oxo-4-phenylcyclohex-1-enecarboxylate was converted to Example 1-06. Mass spectrum 359.13 (M−H$^−$).

Examples 1-07 to 1-30

Examples 1-07 to 1-30 set forth in Table 1 below were prepared using the procedures of Examples 1-01 through 1-06:

TABLE 1

| Example | Compound name | Mass spectrum |
|---|---|---|
| 1-07 | Racemic 6-(2-methoxyphenyl)-6-methyl methylcyclohex-1-enecarboxylic acid | 269.18 (M + Na$^+$) |
| 1-08 | Racemic 6-(3,4-dimethylphenyl)-6-methylcyclohex-1-enecarboxylic acid | 243.23 (M − H$^−$) |
| 1-09 | Racemic 6-(3-chlorophenyl)-6-methylcyclohex-1-enecarboxylic acid | 249.14 (M − H$^−$) |
| 1-10 | Racemic 6-methyl-6-(3-(trifluoromethyl)-phenyl)cyclohex-1-enecarboxylic acid | 283.20 (M − H$^−$) |
| 1-11 | (4RS,6RS)-6-(3,4-dichlorophenyl)-4,6-dimethylcyclohex-1-enecarboxylic acid | 297.05 (M − H$^−$) |
| 1-12 | (4RS,6RS)-4,6-dimethyl-6-(3-(trifluoromethyl)phenyl)cyclohex-1-enecarboxylic acid | 297.18 (M − H$^−$) |
| 1-13 | (4RS,6RS)-6-(4-chloro-3-(trifluoromethyl)-phenyl)-4,6-dimethylcyclohex-1-enecarboxylic acid | 333.13 (M − H$^−$) |
| 1-14 | (4RS,6RS)-6-(3,5-bis(trifluoromethyl)-phenyl)-4,6-dimethylcyclohex-1-enecarboxylic acid | 365.10 (M − H$^−$) |
| 1-15 | (4RS,6RS)-6-(3,4-dimethylphenyl)-4,6-dimethylcyclohex-1-enecarboxylic acid | 281.31 (M + Na$^+$) |
| 1-16 | (4RS,6RS)-4,6-dimethyl-6-(napthalen-1-yl)cyclohex-1-enecarboxylic acid | 303.29 (M + Na$^+$) |
| 1-17 | (4RS,6RS)-4,6-dimethyl-6-p-tolylcyclohex-1-enecarboxylic acid | 267.34 (M + Na$^+$) |
| 1-18 | (4RS,6RS)-4,6-dimethyl-6-m-tolylcyclohex-1-enecarboxylic acid | 267.37 (M + Na$^+$) |
| 1-19 | (4RS,6RS)-6-(2,3-dimethylphenyl)-4,6-dimethylcyclohex-1-enecarboxylic acid | 281.31 (M + Na$^+$) |
| 1-20 | (4RS,6RS)-4,6-dimethyl-6-(naphthalen-2-yl)cyclohex-1-enecarboxylic acid | 303.29 (M + Na$^+$) |
| 1-21 | (4RS,6RS)-6-(4-chlorophenyl)-4,6-dimethylcyclohex-1-enecarboxylic acid | 287.22 (M + Na$^+$) |
| 1-22 | (4RS,6RS)-6-(4-fluorophenyl)-4,6-dimethylcyclohex-1-enecarboxylic acid | 247.26 (M − H$^−$) |
| 1-23 | (4RS,6RS)-6-(3-fluorophenyl)-4,6-dimethylcyclohex-1-enecarboxylic acid | 271.32 (M + Na$^+$) |
| 1-24 | (4RS,6RS)-4,6-dimethyl-6-phenylcyclohex-1-enecarboxylic acid | 253.33 (M + Na$^+$) |
| 1-25 | (4RS,6RS)-6-(4-fluoro-3-methylphenyl)-4,6-dimethylcyclohex-1-enecarboxylic acid | 285.27 (M + Na$^+$) |
| 1-26 | (4RS,6RS)-6-(2,5-dimethylphenyl)-4,6-dimethylcyclohex-1-enecarboxylic acid | 281.31 (M + Na$^+$) |
| 1-27 | (4RS,6RS)-6-(4-chloro-3,5-dimethylphenyl)-4,6-dimethylcyclohex-1-enecarboxylic acid | 315.24 (M + Na$^+$) |
| 1-28 | (4RS,6RS)-4,6-dimethyl-6-(4-methyl-naphthalen-1-yl)cyclohex-1-enecarboxylic acid | 317.31 (M + Na$^+$) |
| 1-29 | (4RS,6RS)-6-(3,5-dimethylphenyl)-4,6-dimethylcyclohex-1-enecarboxylic acid | 281.32 (M + Na$^+$) |
| 1-30 | (4RS,6RS)-6-(3,5-dichlorophenyl)-4,6-dimethylcyclohex-1-enecarboxylic acid | 300.07 (M + H$^+$) |

Example 2

Preparation of (2RS,4SR)-2,4-dimethyl-2-(3-(trifluoromethyl)phenyl)cyclohexanecarboxylic acid A solution of Example 1-12 (8 mg) in methanol (1 mL) was treated with 5% palladium on carbon (1.6 mg). The resulting mixture was stirred under a hydrogen atmosphere at ambient pressure overnight. At the conclusion of this period, the mixture was filtered. The collected solid was washed with methanol and the combined filtrates were concentrated under vacuum to yield Example 2 (6 mg). Mass spectrum 299.20 (M−H$^−$).

Example 3-01

Preparation of (4RS,6RS)-6-(3,4-dichlorophenyl)-4,6-dimethyl-N-(methylsulfonyl)cyclohex-1-enecarboxamide A stirred solution of Example 1-11 (20 mg) in dichloromethane (3 mL) was treated with methanesulfonamide (6.4 mg), EDC hydrochloride (15 mg), and 4-(N,N-dimethylamino)pyridine (10 mg). A small amount of DMF was added to improve solubility, and the mixture was stirred at rt overnight. At the conclusion of this period, the mixture was concentrated under vacuum and the resulting residue was partitioned between ethyl acetate and water. 1 M aqueous HCl was added and the aqueous and organic layers were separated. The aqueous layer was extracted twice with ethyl acetate, and the combined organic layers were washed with saturated aqueous sodium chloride, dried over sodium sulfate and concentrated under vacuum to yield a residue. This residue was purified by preparative HPLC to yield Example 3-01 (4.3 mg). Mass spectrum m/z 376.2 (M+H$^+$).

Examples 3-02 and 3-03

Examples 3-02 and 3-03 set forth in Table 2 below were prepared using the procedures described in Example 3-01:

TABLE 2

| Example | Compound name | Mass spectrum |
|---|---|---|
| 3-02 | (4RS,6RS)-6-(3,4-dichlorophenyl)-4,6-dimethyl-N-(trifluoromethylsulfonyl)-cyclohex-1-enecarboxamide | 452.12 (M + Na$^+$) |
| 3-03 | (4RS,6RS)-6-(3,4-dichlorophenyl)-4,6-dimethyl-N-(phenylsulfonyl)cyclohex-1-enecarboxamide | 438.15 (M + H$^+$) |

Examples 4-01a and 4-01b

Preparation of (4S,6S)-6-(4-chloro-3-(trifluoromethyl)-phenyl)-4,6-dimethylcyclohex-1-enecarboxylic acid and (4R,6R)-6-(4-chloro-3-(trifluoromethyl)phenyl)-4,6-dimethylcyclohex-1-enecarboxylic acid, respectively Chiral preparative HPLC on a Chiralcel OD column was used to separate Example 1-13 into Examples 4-01a and 4-01b.

Examples 4-02a and 4-02b

Preparation of (4S,6S)-6-(3,4-dichlorophenyl)-4,6-dimethylcyclohex-1-enecarboxylic acid and (4R,6R)-6-(3,4-dichlorophenyl)-4,6-dimethylcyclohex-1-enecarboxylic acid, respectively Chiral preparative HPLC on a Chiralcel OJ column was used to separate Example 1-11 into Examples 4-02a and 4-02b.

Example 5

Preparation of (4RS,6SR)-6-(3,4-dichlorophenyl)-6-hydroxy-2,4,-dimethylcyclohex-1-enecarboxylic acid Step 1. A solution of racemic methyl 2,4-dimethyl-6-oxocyclohex-1-enecarboxylate (Example 1-03, Step 4; 100 mg) in THF (5 mL) was treated with 3,4-dichlorophenylmagnesium bromide (0.5 M, 1.3 mL). The mixture was stirred at rt overnight and then treated with saturated aqueous ammonium chloride. The resulting mixture was extracted three times with ethyl acetate. The combined organic layers were washed with saturated aqueous sodium chloride, dried over sodium sulfate and concentrated under vacuum to provide methyl (4RS,6SR)-6-(3,4-dichlorophenyl)-6-hydroxy-2,4,-dimethylcyclohex-1-enecarboxylate (97 mg). Mass spectrum m/z 353.32 (M+Na$^+$).

Step 2. Following the procedure of Step 5, Example 1-01, methyl (4RS,6SR)-6-(3,4-dichlorophenyl)-6-hydroxy-2,4,-dimethylcyclohex-1-enecarboxylate was converted to Example 5. Mass spectrum m/z 313.11 (M−H$^-$).

Example 6

Preparation of (4RS,6RS)-6-(3,4-dichlorophenyl)-2,4,6-trimethylcyclohex-1-enecarboxylic acid Step 1. Using the procedure of Step 1, Example 1-01, racemic methyl 2,4-dimethyl-6-oxocyclohex-1-enecarboxylate (Example 1-03, Step 4) was converted to methyl (2RS,4RS)-2-(3,4-dichlorophenyl)-2,4-dimethyl-6-oxocyclohexane-carboxylate.

Step 2. A stirred suspension of sodium hydride (60% in mineral oil, 13 mg) in diethyl ether (2 mL) was treated at rt with methyl (2RS,4RS)-2-(3,4-dichlorophenyl)-2,4-dimethyl-6-oxocyclohexanecarboxylate (100 mg). The mixture was stirred for 10 min and then a solution of diethyl chlorophosphate in diethyl ether (2 mL) was added. Upon completion of addition, the resulting mixture was stirred at rt for 3 h. After this time, solid ammonium chloride was added and stirring was continued for an additional 30 min. At the conclusion of this period, the resulting suspension was filtered through Celite and the filtrate was concentrated under vacuum to provide methyl (4RS,6SR)-6-(3,4-dichlorophenyl)-2-(diethoxyphosphoryloxy)-4,6-dimethyl-cyclohexen-1-carboxylate in quantitative yield. Mass spectrum m/z 465.19 (M+H$^+$).

Step 3. A stirred suspension of copper (I) iodide (213 mg) in diethyl ether (10 mL) at 0° C. was treated with methyllithium (1.6 M, 1 equivalent), forming a cloudy yellow mixture. Additional methyllithium (1.6 M, 1 equivalent) was added, forming a cloudy grey mixture. This cloudy grey mixture was stirred at 0° C. for 15 min, and then treated with a solution of methyl (4RS,6SR)-6-(3,4-dichlorophenyl)-2-(diethoxyphosphoryloxy)-4,6-dimethylcyclohexen-1-carboxylate (130 mg) in diethyl ether (5 mL). A deep red color formed over 30 min. Stirring was continued while warming to rt for 2 h more. At the conclusion of this period, the resulting mixture was treated with 3:1 saturated aqueous ammonium chloride/concentrated ammonium hydroxide, and stirred for 10 min. The mixture was then extracted three times with diethyl ether, and the combined organic layers were washed with saturated aqueous ammonium chloride and saturated aqueous sodium chloride, dried over magnesium sulfate and concentrated under vacuum. The resulting residue was purified by column chromatography on silica gel, eluting with 15% ethyl acetate/hexanes, to provide methyl (4RS,6RS)-6-(3,4-dichlorophenyl)-2,4,6-trimethylcyclohex-1-enecarboxylate (57 mg). Mass spectrum m/z 349.17 (M+Na$^+$).

Step 4. Following the procedure of Step 7, Example 1-3, (except that potassium hydroxide was used in place of sodium hydroxide), methyl (4RS,6RS)-6-(3,4-dichlorophenyl)-2,4,6-trimethylcyclohex-1-enecarboxylate was converted to Example 6. Mass spectrum m/z 313.14 (M+H$^+$).

Example 7

Preparation of (4RS,6RS)-6-(4-chloro-3-(trifluoromethyl)-phenyl)-4-(hydroxymethyl)-6-methylcyclohex-1-enecarboxylic acid Step 1. A solution of diisopropylamine (3.85 mL, 27.0 mmol) in THF (40 mL) was stirred on an ice bath and treated dropwise with n-butyllithium (1.6 M in hexane, 16.11 mL, 25.8 mmol) over 15 min. The resulting solution was stirred for 10 min, and then cooled to about −75° C. Once at the prescribed temperature, a solution of methyl 2-(4-chloro-3-(trifluoromethyl)phenyl)acetate (6.20 g, 24.54 mmol) in THF (25 mL) was added dropwise. The resulting orange solution was stirred for 30 min, at which time the color had lightened to bright yellow. Additional THF (100 mL) was added, followed by a solution of methyl acrylate (4.89 mL, 54.0 mmol) in THF (50 mL) over a 10 min period. Upon completion of addition, the mixture was stirred at about −75° C. for 17.5 h. After this time, the mixture was treated with saturated aqueous ammonium chloride and warmed to rt. Once at the prescribed temperature, the mixture was diluted with enough water to dissolve the precipitate and then extracted three times with ethyl acetate. The combined organic layers were washed with saturated aqueous sodium chloride, dried over sodium sulfate and concentrated under vacuum to yield a residue. The residue was purified by column chromatography on silica gel, eluting with 15-40% ethyl acetate-hexanes to provide a mixture of diastereomers of dimethyl 5-(4-chloro-3-(trifluoromethyl)phenyl)-4-hydroxycyclohex-3-ene-1,3-dicarboxylate as a pale yellow viscous syrup (6.646 g, 68%). Mass spectrum m/z 393.1 (M+H$^+$).

Step 2. A solution of dimethyl 5-(4-chloro-3-(trifluoromethyl)phenyl)-4-hydroxycyclohex-3-ene-1,3-dicarboxylate (6.610 g, 16.83 mmol) in dimethyl sulfoxide (40 mL) was treated with sodium chloride (1.967 g, 33.7 mmol) and water (1.516 mL, 84 mmol). The resulting mixture was bubbled with argon for 15 min, and then heated under argon at 150-160° C., resulting in gas evolution. After 3 h, the orange mixture was cooled to rt and then diluted with water and ethyl acetate. The layers were mixed thoroughly and separated. The aqueous phase was extracted three times with ethyl acetate. The combined organic layers were washed with water, saturated aqueous sodium chloride, dried over sodium sulfate and concentrated under vacuum to yield a residue. The residue was purified by column chromatography on silica gel, eluting with 20-45% ethyl acetate-hexanes, to provide a mixture of diastereomers of methyl 3-(4-chloro-3-(trifluoromethyl)phenyl)-4-oxocyclohexanecarboxylate as an off-white solid (4.252 g, 75%). Mass spectrum m/z 352.1 (M+NH$_4^+$). The isomers could be separated by careful chromatography, but were normally used without separation. Isomer 1:1H NMR (400 MHz, CDCl$_3$) δ 7.48 (d, J=8.3 Hz, 1 H), 7.46 (d, J=2.0 Hz, 1 H), 7.26 (dd, J=8.3, 2.0 Hz, 1 H), 3.96 (dd, J=12.6, 5.5 Hz, 1 H), 3.82 (s, 3 H), 3.02 (m, 1 H), 2.59 (m, 4 H), 2.16 (m, 2 H). Isomer 2: 1H NMR (400 MHz, CDCl$_3$) δ 7.48 (d, J=8.3 Hz, 1 H), 7.43 (d, J=2.0 Hz, 1 H), 7.25 (dd, J=8.3, 2.3 Hz, 1 H), 3.73 (s, 3 H), 3.71 (dd, J=13.9, 5.0 Hz, 1 H), 3.00 (tt, J=12.3, 3.5 Hz, 1 H), 2.55 (m, 4 H), 2.17 (m, 1 H), 2.04 (m, 1 H).

Step 3a. A solution of diisopropylamine (1.583 mL, 11.11 mmol) in THF (35 mL) was stirred at −10° C. and then treated dropwise with n-butyllithium (1.6 M in hexane, 6.20 mL, 9.92 mmol). Upon completion of addition, the solution was stirred for 10 min and then cooled to about −72° C. Once at the prescribed temperature, the solution was treated dropwise over a 15 min period with a solution of methyl 3-(4-chloro-3-(trifluoromethyl)phenyl)-4-oxocyclohexanecarboxylate (2.656 g, 7.94 mmol) in THF (35 mL). The resulting solution was stirred for 10 min, and then warmed to rt where it stirred for 3.25 h. After this time, the solution was cooled again to about −70° C. and treated dropwise with methyl iodide (0.744 mL, 11.90 mmol). After 5 min the cooling bath was removed and the solution was allowed to warm to rt where it stirred for 19 h. At the conclusion of this period, the mixture was treated with saturated aqueous ammonium chloride and extracted three times with ethyl acetate. The combined organic phases were dried over sodium sulfate and concentrated under vacuum to yield a residue. The residue was purified by column chromatography on silica gel, eluting with 15-40% ethyl acetate-hexanes. The less polar product was methyl (1RS,3RS)-3-(4-chloro-3-(trifluoromethyl)-phenyl)-3-methyl-4-oxocyclohexanecarboxylate isolated as a pale yellow gum (261 mg, 9%). Mass spectrum m/z 366.2 (M+NH$_4^+$). 1H NMR (400 MHz, CDCl$_3$) δ 7.53 (d, J=8.3 Hz, 1 H), 7.49 (d, J=2.0 Hz, 1 H), 7.32 (dd, J=8.3, 2.3 Hz, 1 H), 3.74 (s, 3 H), 2.91 (dt, J=14.7, 3.2, 3.1 Hz, 1 H), 2.81 (m, J=12.6, 12.6, 3.3, 3.3 Hz, 1 H), 2.44 (m, 1 H), 2.33 (m, 1 H), 2.24 (m, 1 H), 2.00 (dd, J=14.6, 12.8 Hz, 1 H), 1.92 (m, 1 H), 1.30 (s, 3 H). The more polar product was methyl (1SR,3RS)-3-(4-chloro-3-(trifluoro-methyl)phenyl)-3-methyl-4-oxocyclohexanecarboxylate, isolated as a pale yellow gum (1.272 g, 46%). Mass spectrum m/z 366.1 (M+NH$_4^+$). 1H NMR (400 MHz, CDCl$_3$) δ 7.55 (d, J=2.3 Hz, 1 H), 7.46 (d, J=8.6 Hz, 1 H), 7.32 (dd, J=8.4, 2.4 Hz, 1H), 3.66 (s, 3 H), 3.01 (m, 1 H), 2.68 (m, 2 H), 2.51 (dd, J=14.1, 10.8 Hz, 1 H), 2.30 (m, 1 H), 2.22 (m, 1 H), 2.09 (m, 1 H), 1.58 (s, 3 H).

Step 3b. Methyl (1SR,3RS)-3-(4-chloro-3-(trifluoromethyl)phenyl)-3-methyl-4-oxocyclohexanecarboxylate (1.233 g, 3.54 mmol) was dissolved in methanol (30 mL) and then treated with sodium methoxide (0.5 M in methanol, 8.49 mL, 4.24 mmol). The resulting mixture was allowed to stand at rt for 23.5 h. After this time, the mixture was treated with 1 M aqueous HCl and concentrated under vacuum to yield a residue. The residue was purified by column chromatography on silica gel, eluting with 15-35% ethyl acetate-hexanes, to provide methyl (1RS,3RS)-3-(4-chloro-3-(trifluoromethyl)phenyl)-3-methyl-4-oxocyclohexanecarboxylate as a colorless gum (644 mg, 51%). Recovered methyl (1SR,3RS)-3-(4-chloro-3-(trifluoromethyl)phenyl)-3-methyl-4-oxocyclohexane-carboxylate (260 mg, 20%) was also obtained as a colorless gum.

Step 4. A solution of methyl (1RS,3RS)-3-(4-chloro-3-(trifluoromethyl)phenyl)-3-methyl-4-oxocyclohexane-carboxylate (1.348 g, 3.87 mmol) in ethanol (20 mL) was treated with sodium borohydride (0.292 g, 7.73 mmol) and stirred at 60° C. Additional sodium borohydride (100 mg) was added after 7 h and again after 22.75 h. After 28 h, the resulting mixture was concentrated under vacuum and the resulting residue was stirred with ethyl acetate and saturated aqueous sodium bicarbonate for 30 min. The aqueous and organic layers were separated and the aqueous phase was extracted with ethyl acetate. The combined organic phases were dried over sodium sulfate and concentrated under vacuum to yield a residue. This residue was purified by column chromatography on silica gel, eluting with 30-70% ethyl acetate-hexanes, to provide (1RS,2RS,4RS)-2-(4-chloro-3-(trifluoromethyl)phenyl)-4-(hydroxymethyl)-2-methylcyclohexanol as a white glassy foam (967 mg, 78%). 1H NMR (500 MHz, CDCl$_3$) δ 8.14 (d, J=2.2 Hz, 1 H), 7.82 (dd, J=8.5, 2.2 Hz, 1 H), 7.41 (d, J=8.8 Hz, 1 H), 3.76 (dd, J=12.1, 3.8 Hz, 1 H), 3.45 (ab portion of abx, 2 H), 2.37 (dt, J=14.3, 2.7 Hz, 1 H), 1.92 (br. s, 1 H), 1.82 (m, 1 H), 1.77 (m, 1 H), 1.58 (m, 3 H), 1.35 (s, 3 H), 1.18 (m, J=14.0, 12.4 Hz, 2H).

Step 5. A solution of (1RS,2RS,4RS)-2-(4-chloro-3-(trifluoromethyl)phenyl)-4-(hydroxymethyl)-2-methylcyclohexanol (1.253 g, 3.88 mmol) in DMF (15 mL) was treated with imidazole (0.581 g, 8.54 mmol) followed by tert-butyldiphenylchlorosilane (1.097 mL, 4.27 mmol). The resulting mixture was stirred at rt for 29 h. After this time, the solution was diluted with ethyl acetate (150 mL), washed three times with water, once with saturated aqueous sodium chloride, dried over sodium sulfate and concentrated under vacuum. The resulting residue was purified by column chromatography on silica gel, eluting with 5-25% ethyl acetate-hexanes, to provide (1RS,2RS,4RS)-4-((tert-butyldiphenylsilyloxy)methyl)-2-(4-chloro-3-(trifluoromethyl)phenyl)-2-methylcyclohexanol as a colorless gummy glass (1.599 g, 73%). 1H NMR (400 MHz, CDCl$_3$) δ 8.14 (s, 1 H), 7.82 (dd, J=8.5, 1.6 Hz, 1 H), 7.63 (t, J=6.6 Hz, 4 H), 7.40 (m, 7 H), 3.72 (dt, J=12.0, 3.5, 3.4 Hz, 1 H), 3.42 (m, 2 H), 2.43 (m, 1 H), 1.69 (m, 5 H), 1.33 (s, 3 H), 1.12 (m, 2 H), 1.06 (s, 9 H).

Step 6. A solution of (1RS,2RS,4RS)-4-((tert-butyldiphenylsilyloxy)methyl)-2-(4-chloro-3-(trifluoromethyl)phenyl)-2-methylcyclohexanol (1.35 g, 2.406 mmol) in dichloromethane (40 mL) was treated with Celite (1.5 g, 24.97 mmol) and pyridinium chlorochromate (0.778 g, 3.61 mmol). The resulting mixture was stirred at rt for 19.5 h, then diluted with Et$_2$O and stirred vigorously at rt. The resulting slurry was filtered through a pad of Florisil and the solids were rinsed thoroughly with Et$_2$O. The filtrate was concentrated under vacuum, taken up in dichloromethane and concentrated. The resulting residue was purified by column chromatography on silica gel, eluting with 0-15% ethyl acetate-hexane, to provide (2RS,4RS)-4-((tert-butyldiphenylsilyloxy)methyl)-2-(4-chloro-3-(trifluoromethyl)phenyl)-2-methylcyclohexanone as a colorless gum (1.338 g, 99%). 1H NMR (400 MHz, CDCl$_3$) δ 7.66 (m, 4 H), 7.53 (d, J=2.0 Hz, 1 H), 7.43 (m, 7 H), 7.26 (m, 1 H), 3.58 (dd, J=9.8, 5.5 Hz, 1 H), 3.48 (dd, J=9.8, 7.1 Hz, 3 H), 2.79 (dt, J=14.6, 3.0 Hz, 1 H), 2.33 (m, 2 H), 2.07 (m, 1 H), 1.93 (m, 1 H), 1.49 (dd, J=14.6, 12.6 Hz, 1 H), 1.41 (m, J=12.5, 4.9 Hz, 1 H), 1.26 (s, 3 H), 1.09 (s, 9 H).

Step 7. A solution of sodium bis(trimethylsilyl)amide (1.0 M in THF, 2.53 mL, 2.53 mmol) was diluted with THF (1.5 mL) and stirred at about −75° C. The solution was treated dropwise with a solution of (2RS,4RS)-4-((tert-butyl-diphenylsilyloxy)methyl)-2-(4-chloro-3-(trifluoromethyl)-phenyl)-2-methylcyclohexanone (708 mg, 1.266 mmol) in THF (4.5 mL) over a 10 min period. Upon completion of addition, the mixture was stirred for 1 h and then a solution of N-(5-chloropyridin-2-yl)-triflimide (Comin's reagent, 994 mg, 2.53 mmol) in THF (4.5 mL) was added over a 5 min period.

The resulting solution was stirred at −75° C. for 25 min. After this time, the solution was allowed to warm to rt where it stirred for 3.75 h. At the conclusion of this period, the solution was treated with saturated aqueous sodium chloride, diluted with ethyl acetate and a small amount of water, and the aqueous and organic layers were separated. The aqueous phase was extracted twice with ethyl acetate, and the combined organic phases were dried over sodium sulfate and concentrated under vacuum to yield a residue. The residue was purified by column chromatography on silica gel, eluting with 0-15% ethyl acetate-hexane, to provide (4RS,6RS)-4-((tert-butyldiphenylsilyloxy)methyl)-6-(4-chloro-3-(trifluoromethyl)phenyl)-6-methylcyclohex-1-enyl trifluoromethanesulfonate as a colorless gum (867 mg, 99%). 1H NMR (400 MHz, CDCl$_3$) δ 7.60 (d, J=2.2 Hz, 1 H), 7.54 (m, 2 H), 7.50 (m, 2 H), 7.46 (d, J=8.6 Hz, 1 H), 7.41 (m, 3 H), 7.33 (m, 4 H), 6.06 (dd, J=5.6, 2.5 Hz, 1 H), 3.43 (m, 2 H), 2.29 (m, 1 H), 2.02 (m, 2 H), 1.66 (t, J=13.0 Hz, 1 H), 1.57 (s, 3 H), 1.51 (m, 1 H), 0.98 (s, 9 H).

Step 8. A solution of (4RS,6RS)-4-((tert-butyldiphenylsilyloxy)methyl)-6-(4-chloro-3-(trifluoromethyl)phenyl)-6-methylcyclohex-1-enyl trifluoromethane-sulfonate (816 mg, 1.086 mmol) in DMF (4.5 mL) was treated with methanol (1.762 mL, 43.4 mmol) and N,N-diisopropylethylamine (0.569 mL, 3.26 mmol), and bubbled with nitrogen for 5 min. The resulting mixture was treated with dppf (48.2 mg, 0.087 mmol) and palladium (II) acetate (19.51 mg, 0.087 mmol). The resulting solution was bubbled with carbon monoxide for 5 min, and then stirred under a carbon monoxide balloon at 60° C. for 6 h. At the conclusion of this period, the mixture was cooled to rt and diluted with ethyl acetate. The resulting mixture was washed with 1 M aqueous HCl, twice with water, once with saturated aqueous sodium chloride, dried over sodium sulfate and then concentrated under vacuum to yield a residue. The residue was purified by column chromatography on silica gel, eluting with 0-15% ethyl acetate-hexane, to provide methyl (4RS,6RS)-4-((tert-butyldiphenylsilyloxy)-methyl)-6-(4-chloro-3-(trifluoromethyl)phenyl)-6-methyl-cyclohex-1-enecarboxylate as a colorless gum (498 mg, 76%). 1H NMR (400 MHz, CDCl$_3$) δ 7.53 (m, 5 H), 7.36 (m, 7 H), 7.26 (m, 2 H), 3.65 (s, 3 H), 3.43 (d, J=5.3 Hz, 2 H), 2.33 (m, 1 H), 1.98 (ddd, J=19.5, 10.4, 2.4 Hz, 8 H), 1.77 (m, 1 H), 1.62 (s, 3 H), 1.48 (m, 2 H), 0.97 (s, 9 H).

Step 9. A solution of methyl (4RS,6RS)-4-((tert-butyl-diphenylsilyloxy)methyl)-6-(4-chloro-3-(trifluoromethyl)-phenyl)-6-methylcyclohex-1-enecarboxylate (495 mg, 0.823 mmol) in THF (5 mL) was treated at rt with acetic acid (0.118 mL, 2.058 mmol), followed by tetrabutylammonium fluoride (1.0 M in THF, 1.235 mL, 1.235 mmol). The resulting solution was stirred for 17.5 h. After this time, the solution was diluted with ethyl acetate, washed sequentially with saturated aqueous sodium bicarbonate, water and saturated aqueous sodium chloride, dried over sodium sulfate and then concentrated under vacuum to yield a residue. The residue was purified by column chromatography on silica gel, eluting with 20-50% ethyl acetate-hexane, to provide methyl (4RS,6RS)-6-(4-chloro-3-(trifluoromethyl)phenyl)-4-(hydroxymethyl)-6-methylcyclohex-1-enecarboxylate as a colorless gum (281 mg, 94%). Mass spectrum m/z 363.0 (M+H$^+$). 1H NMR (400 MHz, CDCl$_3$) δ 7.55 (d, J=2.2 Hz, 1 H), 7.39 (d, J=8.6 Hz, 1 H), 7.32 (dd, J=8.6, 2.2 Hz, 17 H), 7.28 (dd, J=5.4, 2.5 Hz, 1 H), 3.64 (s, 3 H), 3.42 (m, 2 H), 2.45 (m, 1 H), 2.00 (m, 1 H), 1.76 (m, 1 H), 1.65 (s, 3 H), 1.53 (m, 2 H), 1.42 (br. s, 1 H).

Step 10. A solution of methyl (4RS,6RS)-6-(4-chloro-3-(trifluoromethyl)phenyl)-4-(hydroxymethyl)-6-methylcyclohex-1-enecarboxylate (28 mg, 0.077 mmol) in ethanol (1 mL) was treated with 1.0 M aqueous sodium hydroxide (1 mL, 1.000 mmol) and the resulting solution was heated at 95° C. for 2.5 h. After this time, the solution was removed from the heating bath and 1 M aqueous HCl was added (1.3 mL). The resulting solution was cooled and then concentrated to yield a residue. The residue was purified by preparative HPLC and lyophilized to provide Example 7 as a white powder (17 mg, 63%). Mass spectrum m/z 347.1 (M−H$^−$). 1H NMR (400 MHz, CD$_3$OD) δ 7.49 (s, 1 H), 7.41 (m, 2 H), 7.24 (dd, J=5.3, 2.5 Hz, 1 H), 3.23 (m, 2 H), 2.33 (m, J=5.2, 5.2 Hz, 1 H), 1.85 (m, 1 H), 1.75 (m, 1 H), 1.58 (s, 3 H), 1.39 (m, 2H).

Example 8

Alternative preparation of the intermediate methyl (1RS, 3RS)-3-(4-chloro-3-(trifluoromethyl)-phenyl)-3-methyl-4-oxocyclohexanecarboxylate Step 1. A solution of diisopropylamine (2.97 mL, 20.85 mmol) in THF (22 mL) was stirred at 0° C. and treated dropwise with n-butyllithium (1.6 M in hexane, 13.03 mL, 20.85 mmol). The resulting solution was stirred for 5 min, and then was cooled to about −75° C. Once at the prescribed temperature, a solution of methyl 2-(4-chloro-3-(trifluoromethyl)phenyl)acetate (4.39 g, 17.38 mmol) in THF (44 mL) was added dropwise over a 15 min period. The resulting solution was stirred at about −75° C. for 30 min, and then warmed to 0° C. Once at the prescribed temperature, the solution was rapidly treated with methyl iodide (1.630 mL, 26.1 mmol). The resulting solution was stirred for 30 min, treated with 1.0 M aqueous HCl and then extracted three times with ethyl acetate. The combined organic phases were washed with 5% aqueous sodium bisulfite (2×25 mL) followed by saturated aqueous sodium chloride, dried over sodium sulfate and concentrated under vacuum. The resulting residue was purified by column chromatography on silica gel, eluting with 5-15% ethyl acetate-hexane, to provide racemic methyl 2-(4-chloro-3-(trifluoromethyl)-phenyl)propanoate as a colorless oil (3.444 g, 72%). 1H NMR (400 MHz, CDCl$_3$) δ 7.61 (d, J=2.0 Hz, 1 H), 7.47 (d, J=8.4 Hz, 1 H), 7.42 (dd, J=8.4, 2.0 Hz, 1 H), 3.76 (q, J=7.3 Hz, 1 H), 3.68 (s, 3 H), 1.52 (d, J=7.3 Hz, 3 H).

Step 2. A solution of diisopropylamine (1.650 mL, 11.57 mmol) in THF (12 mL) was stirred at about 0° C. and treated over a 5 min period with n-butyllithium (1.6 M in hexanes, 6.68 mL, 10.68 mmol). The resulting mixture was stirred for 10 min, and then was cooled to about −70° C., where it was treated dropwise over a 10 min period with a solution of racemic methyl 2-(4-chloro-3-(trifluoromethyl)-phenyl)propanoate (2.374 g, 8.90 mmol) in THF (24 mL). The resulting solution was stirred below −70° C. for 60 min, and then treated dropwise with a solution of methyl acrylate (3.23 mL, 35.6 mmol) in THF (16 mL) over a 5 min period. This solution was stirred overnight while allowing to warm to rt. After 22.5 h, the mixture was treated with saturated aqueous ammonium chloride, and then made acidic with 1 M aqueous HCl. The acidic mixture was extracted three times with ethyl acetate. The combined organic layers were dried over sodium sulfate and concentrated under vacuum to yield a residue. The residue was purified by column chromatography on silica gel, eluting with 10-20% ethyl acetate-hexanes, to provide dimethyl 5-(4-chloro-3-(trifluoromethyl)phenyl)-4-hydroxy-5-methylcyclohex-3-ene-1,3-dicarboxylate as a colorless gum (1.294 g, 36%) which was a mixture of diastereomers by NMR. Mass spectrum m/z 405.0 (M−H$^−$). 1H NMR (400 MHz, CDCl$_3$) δ 12.56 (s, 1 H), 12.36 (s, 1 H), 7.60 (dd, J=8.2, 2.1 Hz, 2 H), 7.45 (d, J=8.6 Hz, 2 H), 7.39 (dt, J=8.3, 2.4 Hz, 2 H), 3.84 (s, 3 H), 3.83 (s, 3 H), 3.65 (s, 3 H), 3.64 (s, 3 H), 2.76 (m, 3 H), 2.53 (dd, J=17.1, 12.1 Hz, 1 H), 2.41 (dd, J=16.0, 11.4 Hz, 1 H), 2.25 (m, 2 H), 2.00 (m, 3 H), 1.72 (s, 3 H), 1.60 (s, 3 H).

Step 3. A solution of dimethyl 5-(4-chloro-3-(trifluoromethyl)phenyl)-4-hydroxy-5-methylcyclohex-3-ene-1,3-dicarboxylate (mixture of diastereomers, 485 mg, 1.192 mmol) in DMSO (5 mL) was treated with sodium chloride (139 mg, 2.385 mmol) and water (0.107 mL, 5.96 mmol). The resulting mixture was bubbled with nitrogen for 15 min, and then heated under nitrogen on an oil bath at 150-160° C. for 4.5 h. After this time, the mixture was cooled to rt, diluted with water and then extracted three times with ethyl acetate. The combined organic layers were washed with water followed by saturated aqueous sodium chloride, dried over sodium sulfate and concentrated under vacuum to yield a residue. The residue was purified by column chromatography on silica gel, eluting with 20-35% ethyl acetate-hexanes, to provide methyl (1RS,3RS)-3-(4-chloro-3-(trifluoromethyl)-phenyl)-3-methyl-4-oxocyclohexanecarboxylate (137 mg, 33%) and methyl (1SR,3RS)-3-(4-chloro-3-(trifluoro-methyl)phenyl)-3-methyl-4-oxocyclohexanecarboxylate (188 mg, 45%). The (1SR, 3RS) diastereomer could be partially converted to the (1RS, 3RS) diastereomer as described in the procedure of Example 7, Part 3.

Example 9

Preparation of (4RS,6RS)-6-(4-chloro-3-(trifluoromethyl)-phenyl)-4-(hydroxymethyl)-6-methylcyclohex-1-enecarboxylic acid Step 1. A solution of methyl (4RS,6RS)-6-(4-chloro-3-(trifluoromethyl)phenyl)-4-(hydroxymethyl)-6-methylcyclohex-1-enecarboxylate (Example 7, Step 9; 32.2 mg, 0.089 mmol) in DMF (0.25 mL) was diluted with methyl iodide (0.75 mL, 11.99 mmol) and treated with silver oxide (103 mg, 0.444 mmol). The resulting suspension was protected from ambient light and stirred at rt for 41.5 h. After this time, the mixture was diluted with ethyl acetate, washed with water, dried over sodium sulfate and concentrated under vacuum. The resulting residue was purified by column chromatography on silica gel, eluting with 10-30% ethyl acetate-hexanes, to provide methyl (4RS,6RS)-6-(4-chloro-3-(trifluoromethyl)phenyl)-4-(methoxymethyl)-6-methylcyclohex-1-enecarboxylate as a colorless gum (20 mg, 60%). Mass spectrum m/z 394.1 (M+NH$_4^+$). 1H NMR (400 MHz, CDCl$_3$) δ 7.55 (d, J=2.2 Hz, 1 H), 7.38 (d, J=8.4 Hz, 1 H), 7.31 (dd, J=8.4, 2.2 Hz, 1 H), 7.27 (m, 1 H), 3.64 (s, 3 H), 3.24 (s, 3 H), 3.15 (d, J=5.7 Hz, 2 H), 2.44 (m, 1 H), 2.00 (ddd, J=19.5, 10.4, 2.4 Hz, 1 H), 1.74 (m, 1 H), 1.65 (s, 3 H), 1.61 (m, 1 H), 1.56 (m, 1H).

Step 2. A solution of methyl (4RS,6RS)-6-(4-chloro-3-(trifluoromethyl)phenyl)-4-(methoxymethyl)-6-methylcyclohex-1-enecarboxylate (20 mg, 0.053 mmol) in ethanol (1 mL) was treated with 1.0 M aqueous sodium hydroxide (1 mL, 1.00 mmol). The resulting mixture was heated to 95° C. where it stirred for 2.5 h. After this time, the mixture was cooled to rt, acidified with 1 M aqueous HCl (1.1 mL), purified by preparative HPLC and then lyophilized to provide Example 9 as a white powder (13.4 mg, 70%). Mass spectrum m/z 380.0 (M+NH$_4^+$). 1H NMR (400 MHz, CDCl$_3$) δ 7.53 (d, J=2.2 Hz, 1 H), 7.41 (dd, J=5.3, 2.4 Hz, 1 H), 7.38 (d, J=8.6 Hz, 1 H), 7.30 (dd, J=8.5, 2.1 Hz, 1 H), 3.24 (s, 3 H), 3.15 (d, J=5.3 Hz, 2 H), 2.46 (dt, J=20.6, 4.7 Hz, 1 H), 2.02 (ddd, J=19.8, 9.9, 2.1 Hz, 1 H), 1.74 (m, 1 H), 1.67 (s, 3 H), 1.58 (m, 2 H).

Example 10

Preparation of (4RS,6RS)-4-(tert-butoxymethyl)-6-(4-chloro-3-(trifluoromethyl)phenyl)-6-methylcyclohex-1-enecarboxylic acid Step 1. A solution of methyl (4RS,6RS)-6-(4-chloro-3-(trifluoromethyl)phenyl)-4-(hydroxymethyl)-6-methylcyclohex-1-enecarboxylate (Example 7, Step 9; 36.7 mg, 0.101 mmol) in dichloromethane (2 mL) was placed in a sealable tube, treated with p-toluenesulfonic acid hydrate (96 mg, 0.506 mmol) and cooled on dry ice. Liquid isobutylene (1-2 mL) was added, the tube was sealed and the mixture was stirred at rt for 72 h. After this time, the tube was cooled and unsealed, and the isobutylene was allowed to evaporate. The resulting mixture was diluted with dichloromethane, washed with saturated aqueous sodium bicarbonate, dried over sodium sulfate and concentrated under vacuum to yield a residue. The residue was purified by column chromatography on silica gel, eluting with 5-25% ethyl acetate-hexane, to provide methyl (4RS,6RS)-4-(tert-butoxymethyl)-6-(4-chloro-3-(trifluoro-methyl)phenyl)-6-methylcyclohex-1-enecarboxylate (22 mg, 52%). Mass spectrum m/z 436.0 (M+NH$_4^+$). 1H NMR (400 MHz, CDCl$_3$) δ 7.55 (d, J=2.2 Hz, 1 H), 7.37 (d, J=8.6 Hz, 1 H), 7.30 (dd, J=8.4, 2.2 Hz, 1 H), 7.27 (dd, J=5.5, 2.9 Hz, 1 H), 3.64 (s, 3 H), 3.15 (dd, J=8.8, 4.4 Hz, 1 H), 3.07 (dd, J=8.6, 6.4 Hz, 1 H), 2.47 (m, 1 H), 1.96 (m, 1 H), 1.69 (m, 1 H), 1.64 (s, 3 H), 1.54 (m, 2 H), 1.11 (s, 9 H).

Step 2. A solution of methyl (4RS,6RS)-4-(tert-butoxymethyl)-6-(4-chloro-3-(trifluoromethyl)phenyl)-6-methylcyclohex-1-enecarboxylate (24 mg, 0.057 mmol) in ethanol (1 mL) was treated with 1 M aqueous sodium hydroxide (1 mL, 1.000 mmol). The resulting mixture was heated at 90° C. for 2 h. After this time, the mixture was cooled to rt, neutralized with 1.0 M aqueous HCl (1 mL), purified by preparative HPLC, and then lyophilized to provide Example 10 as a white amorphous solid (15.0 mg, 65%). Mass spectrum m/z 422.0 (M+NH$_4^+$). 1H NMR (400 MHz, CDCl$_3$) δ 7.53 (d, J=2.3 Hz, 1 H), 7.41 (dd, J=5.5, 2.5 Hz, 1 H), 7.37 (d, J=8.3 Hz, 1 H), 7.29 (dd, J=8.4, 2.1 Hz, 1 H), 3.15 (dd, J=8.8, 4.8 Hz, 1 H), 3.07 (dd, J=8.8, 6.5 Hz, 1 H), 2.49 (m, 1 H), 1.99 (ddd, J=20.0, 10.1, 2.4 Hz, 1 H), 1.70 (m, 1 H), 1.66 (s, 3 H), 1.53 (m, 2 H), 1.10 (s, 9 H).

Example 11

Preparation of (4RS,6RS)-4-(acetamidomethyl)-6-(4-chloro-3-(trifluoromethyl)phenyl)-6-methylcyclohex-1-enecarboxylic acid Step 1. A solution of methyl (4RS,6RS)-6-(4-chloro-3-(trifluoromethyl)phenyl)-4-(hydroxymethyl)-6-methylcyclohex-1-enecarboxylate (Example 7, Step 9; 38.2 mg, 0.105 mmol) in THF (0.8 mL) was treated sequentially with triphenylphosphine (83 mg, 0.316 mmol), hydrazoic acid (ca. 2M in benzene, 0.211 mL, 0.421 mmol) and diethyl azodicarboxylate (0.050 mL, 0.316 mmol). The resulting mixture was stirred at rt for 19.5 h and then an additional amount of triphenylphosphine (83 mg, 0.316 mmol), diethyl azodicarboxylate (0.050 mL, 0.316 mmol) and hydrazoic acid (ca. 2M in benzene, 0.211 mL, 0.421 mmol) were added. The resulting mixture was stirred for a total of 43 h. After this time, the mixture was concentrated under vacuum to yield a residue. The residue was purified by column chromatography on silica gel, eluting with 5-50% ethyl acetate-hexanes, to provide methyl (4RS,6RS)-4-(azidomethyl)-6-(4-chloro-3-(trifluoromethyl)-phenyl)-6-methylcyclohex-1-enecarboxylate (21 mg, 51%). Mass spectrum m/z 405.0 (M+NH$_4^+$). 1H NMR (400 MHz, CDCl$_3$) δ 7.54 (d, J=2.4 Hz, 1 H), 7.40 (d, J=8.4 Hz, 1 H), 7.31 (dd, J=8.4, 2.4 Hz, 1 H), 7.25 (dd, J=5.5, 2.4 Hz, 1 H), 3.65 (s, 3 H), 3.17 (d, J=5.3 Hz, 2 H), 2.45 (m, 1 H), 2.01 (m, 1 H), 1.73 (m, 1 H), 1.66 (s, 3 H), 1.58 (m, 2 H).

Step 2. A solution of methyl (4RS,6RS)-4-(azidomethyl)-6-(4-chloro-3-(trifluoromethyl)phenyl)-6-methylcyclohex-1-enecarboxylate (21 mg, 0.054 mmol) in THF (0.5 mL) was treated with water (25 μL, 1.388 mmol) followed by triphenylphosphine (15.62 mg, 0.060 mmol). The resulting mixture was stirred at rt for 21.5 h and then concentrated under vacuum to yield a residue. The residue was dissolved in dichloromethane (0.5 mL) and the resulting solution was treated with triethylamine (0.030 mL, 0.217 mmol), dmap (3.31 mg, 0.027 mmol) and acetic anhydride (10.22 μL, 0.108 mmol). The resulting mixture was stirred at rt for 2 h and then concentrated under vacuum to yield a residue. This residue was purified by column chromatography on silica gel, eluting with 60-100% ethyl acetate-hexanes, to provide methyl (4RS,6RS)-4-(acetamidomethyl)-6-(4-chloro-3-(trifluoro-methyl)phenyl)-6-methylcyclohex-1-enecarboxylate (27 mg, estimated 68% yield), which was used in the next step without further purification despite being contaminated with about 45% by weight of triphenylphosphine oxide.

Step 3. A solution of crude methyl (4RS,6RS)-4-(acetamidomethyl)-6-(4-chloro-3-(trifluoromethyl)phenyl)-6-methylcyclohex-1-enecarboxylate (27 mg, 0.037 mmol; containing almost 1 equivalent of triphenylphosphine oxide) in ethanol (1 mL) was treated with 1.0 M aqueous sodium hydroxide (1 mL, 1.000 mmol). The resulting mixture was heated to 90° C. where it stirred for 1.75 h. After this time, the mixture was cooled to rt, acidified with 1.0 M aqueous HCl, purified by preparative HPLC, and lyophilized to provide Example 11 as a fluffy white powder (10.5 mg, 73%). Mass spectrum m/z 407.0 (M+NH$_4^+$). 1H NMR (400 MHz, CD$_3$OD) δ 7.48 (s, 1 H), 7.40 (d, J=1.3 Hz, 2 H), 7.22 (dd, J=5.4, 2.4 Hz, 1 H), 2.90 (m, 2 H), 2.33 (m, 1 H), 1.83 (m, 1 H), 1.75 (s, 3 H), 1.69 (m, 1 H), 1.57 (s, 3 H), 1.42 (m, 2 H).

Example 12

Preparation of (4RS,6RS)-4-(benzyloxy)-6-(4-chloro-3-(trifluoromethyl)phenyl)-6-methylcyclohex-1-enecarboxylic acid Step 1. A solution of 5-bromo-2-chloro-1-trifluoromethylbenzene (1.09 mL, 7.34 mmol) in THF (20 mL) was stirred at −78° C. and treated with n-butyllithium (1.6 M in hexane, 4.59 mL, 7.34 mmol). The resulting solution was stirred at −78° C. for 30 min and then treated with boron trifluoride etherate (924 μL, 7.34 mmol). After stirring for an additional 10 min, a solution of (1RS,3RS,6SR)-3-(benzyloxy)-7-oxabicyclo[4.1.0]heptane (prepared according to the procedure of Chini et al., *J. Org. Chem.* 1990, 55, 4265; 1.00 g, 4.90 mmol) in THF (4.0 mL) was added over a 5 min period. Upon completion of addition, the mixture was stirred at −78° C. for 70 min and then poured into saturated aqueous ammonium chloride. This mixture was extracted three times with ethyl acetate, and the combined organic phases were dried over sodium sulfate and concentrated under vacuum to yield a residue. The residue was purified by column chromatography on silica gel, eluting with 20-60% ethyl acetate-hexanes, to provide (1SR,2RS,4RS)-4-(benzyloxy)-2-(4-chloro-3-(trifluoro-methyl)phenyl)cyclohexanol as a colorless gum (958 mg, 51%). 1H NMR (400 MHz, CDCl$_3$) δ 1.40 (bd, J=3.6 Hz, 1 H) 1.50-1.64 (m, 2 H) 1.82-1.97 (m, 2 H) 2.05-2.12 (m, 1 H) 2.12-2.20 (m, 1 H) 2.95-3.05 (m, 1 H) 3.65-3.74 (m, 1 H) 3.74-3.80 (m, 1 H) 4.54 (ab, J=12.2 Hz, 2 H) 7.27-7.40 (m, 6 H) 7.45 (d, J=8.7 Hz, 1 H) 7.55 (d, J=2.0 Hz, 1 H).

Step 2. A solution of (1SR,2RS,4RS)-4-(benzyloxy)-2-(4-chloro-3-(trifluoromethyl)phenyl)cyclohexanol (923 mg, 2.40 mmol) in dichloromethane (15 mL) was treated with Celite (1.00 g) followed by pyridinium chlorochromate (776 mg, 3.60 mmol). The resulting mixture was stirred at rt for 4.5 h. After this time, the mixture was diluted with ether. The resulting mixture was stirred, triturated, and then filtered through a pad of Florisil. The collected solids were rinsed thoroughly with Et$_2$O. The filtrate was concentrated under vacuum, and the resulting residue was purified by column chromatography on silica gel, eluting with 10-30% ethyl acetate-hexanes, to provide recovered starting material (130 mg, 14%) and (2RS,4RS)-4-(benzyloxy)-2-(4-chloro-3-(trifluoromethyl)phenyl)cyclohexanone as a colorless gum (678 mg, 74%; 86% based on recovered starting material). 1H NMR (400 MHz, CDCl$_3$) δ ppm 1.95 (m, 1 H) 2.08 (td, J=13.7, 2.5 Hz) 2.38-2.55 (m, 3 H) 2.91 (td, J=14.8, 6.1 Hz, 1 H) 3.99 (m, 1 H) 4.13 (dd, J=13.5, 5.3 Hz, 1 H) 4.66 (ab, J=11.7 Hz, 2 H) 7.22 (dd, J=8.1, 2.0 Hz, 1 H) 7.30-7.43 (m, 6 H) 7.45 (d, J=8.7 Hz, 1 H).

Step 3. A solution of lithium bis(trimethylsilyl)amide (1.0 M in THF, 784 μL, 784 μmol) was diluted with THF (3 mL) and stirred at −78° C. A solution of (2RS,4RS)-4-(benzyloxy)-2-(4-chloro-3-(trifluoromethyl)phenyl)cyclohexanone (300 mg, 784 μmol) in THF (2 mL) was added dropwise, and the resulting mixture was stirred at −78° C. for 10 min. After this time the solution was warmed to rt where it stirred for 3 h. At the conclusion of this period, the solution was cooled again to −78° C. and then treated with iodomethane (98 μL, 1.57 mmol). The resulting mixture was warmed to rt where it stirred for 20 h. After this time, the solution was diluted with ethyl acetate, washed with saturated aqueous ammonium chloride followed by saturated aqueous sodium chloride containing a small amount of 1.0 M aqueous HCl, dried over sodium sulfate and concentrated under vacuum. The resulting residue was purified by column chromatography on silica gel, eluting with 15-30% ethyl acetate-hexanes, to provide two products. The less polar was (2RS,4RS)-4-(benzyloxy)-2-(4-chloro-3-(trifluoromethyl)phenyl)-2-methylcyclohexanone, isolated as a colorless syrup (116 mg, 37%). 1H NMR (400 MHz, CDCl$_3$) δ 1.30 (s, 3 H) 1.79 (m, 1 H) 1.90 (dd, J=14.2, 11.2 Hz, 1 H) 2.26 (m, 2 H) 2.43 (m, 1 H) 2.85 (dt, J=14.24, 3.31, 3.3 Hz, 1 H) 3.78 (m, 1 H) 4.61 (ab, J=12.2 Hz, 2 H) 7.14 (dd, J=8.4, 2.3 Hz, 1 H) 7.30-7.43 (m, 6 H) 7.47 (d, J=2.0 Hz, 1 H). The more polar product was (2SR,4RS)-4-(benzyloxy)-2-(4-chloro-3-(trifluoromethyl)phenyl)-2-methylcyclohexanone, isolated as a colorless syrup (130 mg, 42%). 1H NMR (400 MHz, CDCl$_3$) δ 1.40 (s, 3 H) 2.03-2.20 (m, 3 H) 2.44-2.53 (m, 1 H) 2.67-2.79 (m, 2 H) 3.95 (m, 1 H) 4.47 (ab, J=12.2 Hz, 2 H) 7.06-7.12 (m, 2 H) 7.25-7.41 (m, 5 H) 7.63 (d, J=2.0 Hz, 1 H).

Step 4. A solution of (2RS,4RS)-4-(benzyloxy)-2-(4-chloro-3-(trifluoromethyl)phenyl)-2-methylcyclohexanone (99 mg, 0.249 mmol) and N-phenylbis(trifluoromethanesulfonimide) (267 mg, 0.748 mmol) in THF (4.0 mL) was stirred at −78° C. and treated dropwise over about a 5 min period with potassium bis(trimethylsilyl)amide (0.5 M in toluene, 1.50 mL, 0.748 mmol). The resulting solution was stirred at −78° C. for 70 min, and then warmed to rt where it stirred for 2 h. After this time, saturated aqueous sodium chloride was added, and the resulting mixture was diluted with Et$_2$O. The aqueous and organic layers were separated. The aqueous phase was extracted again with Et$_2$O, and the combined organic phases were dried over sodium sulfate and concentrated under vacuum to yield a residue. The residue was purified by column chromatography on silica gel, eluting with 5-25% ethyl acetate-hexanes, to provide (4RS,6RS)-4-(benzyloxy)-6-(4-chloro-3-(trifluoromethyl)phenyl)-6-methylcyclohex-1-enyl trifluoromethanesulfonate as colorless viscous syrup (92 mg, 69%). 1H NMR (400 MHz, CDCl$_3$) δ 1.61 (s, 3 H) 1.98 (dd, J=12.7, 11.2 Hz, 1 H) 2.19 (m, 1 H) 2.34 (ddd, J=17.3, 8.9, 2.8 Hz, 1 H) 2.66 (m, 1 H) 3.37 (m, 1 H) 4.39 (s, 2 H) 5.98 (dd, J=5.6, 3.1 Hz, 1 H) 7.14 (m, 2 H) 7.23-7.48 (m, 5 H) 7.57 (d, J=2.0 Hz, 3 H).

Step 5. A solution of (4RS,6RS)-4-(benzyloxy)-6-(4-chloro-3-(trifluoromethyl)phenyl)-6-methylcyclohex-1-enyl trifluoromethanesulfonate (91 mg, 0.172 mmol) in DMF (1 mL) was treated with triphenylphosphine (9 mg, 34 μmol), methanol (279 μl, 6.88 mmol) and triethylamine (48 μl, 344 μmol). The resulting mixture was bubbled with nitrogen for 5 min and then palladium (II) acetate (4 mg, 17 μmol) was added. Upon completion of addition, the resulting solution was bubbled with carbon monoxide for 5 min and then stirred under a carbon monoxide balloon at 70° C. for 23 h. After this time, the mixture was cooled to rt and diluted with ether. The resulting mixture was washed twice with water and once with saturated aqueous sodium chloride, dried over sodium sulfate and concentrated under vacuum to yield a residue. The residue was purified by column chromatography on silica gel, eluting with 5-50% ethyl acetate-hexanes, to provide methyl (4RS,6RS)-4-(benzyloxy)-6-(4-chloro-3-(trifluoromethyl) phenyl)-6-methylcyclohex-1-enecarboxylate as a yellow gum (59 mg, 78%). Mass spectrum m/z 456 (M+NH$_4^+$), 492 (M+OAc$^-$). 1H NMR (400 MHz, CDCl$_3$) δ 1.68 (s, 3 H) 1.80 (dd, J=12.7, 11.2 Hz, 1 H) 1.98-2.06 (dm, J=12.7 Hz, 1 H) 2.28 (ddd, J=19.0, 9.0, 3.1 Hz, 1 H) 2.65-2.74 (dtd, J=18.8, 5.1, 1.5 Hz, 1 H) 3.28-3.37 (m, 1 H) 3.63 (s, 3 H) 4.32-4.41 (ab, J=11.7 Hz, 2 H) 7.11-7.14 (m, 2 H) 7.16 (dd, J=5.3, 2.8 Hz, 1 H) 7.21-7.28 (m, 3H) 7.32-7.40 (m, 2 H) 7.49 (d, J=2.0 Hz, 1 H).

Step 6. A solution of methyl (4RS,6RS)-4-(benzyloxy)-6-(4-chloro-3-(trifluoromethyl)phenyl)-6-methylcyclohex-1-enecarboxylate (46 mg, 105 μmol) in ethanol (2 mL) was treated with a 1.0 M aqueous solution of sodium hydroxide (2 mL, 2 mmol) and then heated at reflux for 60 min. After this time, the solution was cooled to rt and the ethanol was removed to yield a residue. The residue was diluted with water and acidified with 1.0 M aqueous HCl. The acidified mixture was extracted twice with ethyl acetate, and the combined organic phases were dried over sodium sulfate and concentrated under vacuum. The resulting residue was purified by column chromatography on silica gel, eluting with 40-90% ethyl acetate-hexanes, to provide Example 12 as a pale yellowish gum (34 mg, 76%). Mass spectrum m/z 423 (M−H$^-$). 1H NMR (400 MHz, CDCl$_3$) δ 1.70 (s, 3 H) 1.80 (dd, J=12.7, 11.2 Hz, 1 H) 2.02 (m, 1 H) 2.30 (ddd, J=19.3, 8.9, 2.8 Hz, 1 H) 2.71 (m, 1 H) 3.31 (m, 1 H) 4.36 (ab, J=11.7 Hz, 2 H) 7.09-7.14 (m, 2 H) 7.21-7.31 (m, 6 H) 7.48 (d, J=2.5 Hz, 1 H).

Utility

In general, compounds of the present invention, such as particular compounds disclosed in the preceding examples, have been shown to be modulators of chemokine receptor activity (for example, by displaying Ki values <10,000 nM in a binding assay such as those set forth below). By displaying activity as modulators of chemokine receptor activity, compounds of the present invention are expected to be useful in the treatment of human diseases associated with chemokines and their cognate receptors.

Antagonism of MCP-1 Binding to Human PBMC
(Yoshimura et al., *J. Immunol.* 1990, 145, 292)

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 pM radioligand) and 50 μl of binding buffer containing 5×10$^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx
(Sullivan et al., *Methods Mol. Biol.* 1999, 114, 125-133)

Calcium mobilization is measured using the fluorescent Ca$^{2+}$ indicator dye, Fluo-3. Cells are incubated at 8×10$^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., *J. Immunol. Methods* 1990, 36, 89-97 or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of 2-4×10$^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

THP-1 Monocytic Cell Binding: Whole Cell-based Assay

The human CCR2 binding assay was also established with the THP-1 human monocytic leukemic cell line, which expresses endogenous CCR2, using $^{125}$I-human MCP-1 as the tracer ligand. Radioligand competition binding assays were used for assessment of binding affinity of test compounds to the CCR2 receptor. For radioligand competition studies, 100 μl containing 2.5×10$^5$ THP-1 cells/well (in assay buffer containing 50 mM HEPES, pH7.4, 5 mM MgCl$_2$, 1 mM CaCl$_2$ and 0.5% BSA) were added to 96-well assay plates containing the test compounds in 3-fold serial dilution, with final concentrations ranging from 5 μM to 100 pM. Subsequently, 50 μl $^{125}$I-MCP-1 radioligand at a final concentration of 0.2 nM in assay buffer were added to the reaction. After a 90 minute incubation period at room temperature, the binding reaction was terminated by harvesting on GF/B filter plates (PerkinElmer Cat. No. 6005177) followed by washing with ice-cold wash buffer (50 mM HEPES, pH 7.4, 0.1% BSA, 0.5 M NaCl) to remove unbound ligand. After washing, the plate was dried for 45 minutes at 60° C. followed by addition of 40 μl MicroScint 20 scintillation fluid, sealed and analyzed by the Packard TopCount reader. Non-specific binding was determined in the presence of 10 μM (a molar excess of 5000 fold) of an in-house CCR2 small molecule antagonist (CCR2 IC50=2 nM). Specific binding of $^{125}$I-MCP-1 was calculated as the difference between total and non-specific binding. The competition data was plotted as a percentage inhibition of radioligand specific bound in the absence of test compound (percent of total signal). After correcting for non-specific binding, IC50 values were determined. The IC50 is defined as the concentration of test compound required to reduce $^{125}$I-MCP-1 specific binding by 50% and was calculated using the four parameter logistic equation to fit the normalized data.

Antagonism of MCP-1-Induced Human PBMC Chemotaxis (Bacon et al., *Brit. J. Pharmacol.* 1988, 95, 966)

Neuroprobe MBA96-96-well chemotaxis chamber, Polyfiltronics MPC 96 well plate, and Neuroprobe polyvinylpyrrolidone-free polycarbonate PFDS 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at 1×10$^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell Derivation and Cell Culture

A pool of HT1080 cells stably expressing endogenous CC chemokine receptor 5 (CCR5) were developed using the methods outlined by Harrington, Sherf, and Rundlett (see U.S. Pat. Nos. 6,361,972 and 6,410,266). The highest-expressing clones were isolated using repetitive flow cytometry, followed by sub-cloning. These cells were then cultured in 6-well dishes at 3×10$^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/ glutamine, and 500 microgram/mL hygromycin B (final concentration) at 37° C. with 5% $CO_2$ in a humidified atmosphere.

Membrane Preparation

A cell pellet containing $1\times10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding Assay

The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of [$^{125}$I]-MIP-1 beta (Perkin Elmer; material was diluted in Binding buffer such that the addition of 50 microliters/well gives a final concentration of 0.1 nM [$^{125}$I]-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-based Functional Assay

HT1080 cells (clone 3559.1.6) were plated at 10,000 cells/well (30 microliters) in 384-well plates (black/clear bottom Biocoat PDL, Beckton Dickinson) and charged with 30 microliters/well of Fluoro-4 AM fluorescent dye (prepared by dissolving 1 mg Fluoro-4 AM in 440 microliters DMSO and diluting with 100 microliters of pluronic solution before diluting further with 10 mL of Hanks buffer). The cells were incubated at 37° C. with 5% $CO_2$ for 30 mM before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e., agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

At least one compound of the disclosure is an inhibitor of both CCR2 and CCR5 and may be used to treat diseases associated with either chemokine. These compounds of the present invention are considered dual antagonists.

Compounds of the present invention were tested in one of the assays described immediately above and the results shown in Table 3 below were obtained.

TABLE 3

| Example | CCR2 Binding Ki, nM (n = 1 unless otherwise noted) |
|---|---|
| 1-01 | 440 |
| 1-02 | 3400 |
| 1-03 | 250 |
| 1-04 | 69 |
| 1-05 | 3500 |
| 1-06 | 3900 |
| 1-07 | 10000 |
| 1-08 | 8200 |
| 1-09 | 3000 |
| 1-10 | 1600 |
| 1-11 | 80 |
| 1-12 | 280 |
| 1-13 | 11 |
| 1-14 | 740 |
| 1-15 | 330 |
| 1-16 | 140 |
| 1-17 | 2600 |
| 1-18 | 930 |
| 1-19 | 3700 |
| 1-20 | 320 |
| 1-21 | 900 |
| 1-22 | 480 |
| 1-23 | 3700 |
| 1-24 | 1000 |
| 1-25 | 1100 |
| 1-26 | 550 |
| 1-27 | 130 |
| 1-28 | 250 |
| 1-29 | 300 |
| 1-30 | 110 |
| 2 | 5800 |
| 3-01 | 5400 |
| 3-02 | 6600 |
| 3-03 | 150 |
| 4-01a | 9 |
| 4-01b | 4500 |
| 4-02a | 36 |
| 4-02b | 5800 |
| 5 | 1000 |
| 6 | 580 |
| 7 | 210 |
| 9 | 310 |
| 10 | 6200 |
| 11 | 5500 |
| 12 | 2500 |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostoma braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, hemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthes parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage And Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences* (Mack Publishing Company), a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of formula (I):

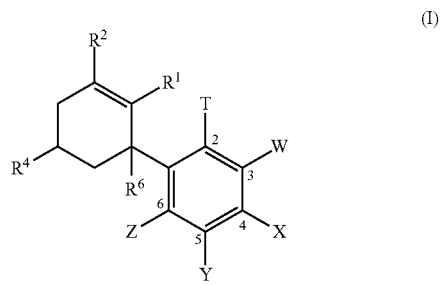

or a stereoisomer or a pharmaceutically acceptable salt thereof, wherein:

$R^1$ is selected from —COOH or —C(=O)NHSO$_2$R$^{12}$;

$R^2$ is H or $C_{1-6}$ alkyl;

$R^4$ is H, $C_{1-4}$ alkyl, $C_{1-4}$ alkoxy, or aryl wherein the $C_{1-4}$ alkyl, $C_{1-4}$ alkoxy and aryl may be optionally substituted with one or more $R^{4a}$'s;

$R^{4a}$ is independently —OH, $C_{1-4}$ alkoxy, —NHC(=O) $C_{1-6}$ alkyl, aryl, or aryloxy;

$R^6$ is selected from H, —OH or $C_{1-4}$ alkyl;

$R^{12}$ is $C_{1-6}$ alkyl, halo$C_{1-6}$ alkyl or aryl;

T is H, $C_{1-4}$ alkyl, halo$C_{1-4}$ alkyl, $C_{1-4}$ alkoxy, or halo;

W is H, $C_{1-4}$ alkyl, halo$C_{1-4}$ alkyl, halo or aryl;

X is H, $C_{1-4}$ alkyl, $C_{1-4}$ alkoxy, or halo;

Y is H, $C_{1-4}$ alkyl, halo$C_{1-4}$ alkyl, $C_{1-4}$ alkoxy, halo or aryl;

Z is selected from H, Cl, $C_{1-2}$ alkyl and $C_{1-2}$ alkoxy;

or alternatively any two adjacent T, W, X, Y and Z can be taken together to form a fused cycloalkyl, heteroaryl, heterocyclyl ring, which may be optionally substitute with one or more $R^{4a}$'s;

provided that:

(1) $R^2$, $R^4$, T, W, X, Y and Z are not all H;

(2) X is not propyl or t-butyl when $R^2$, T, W, X, Y and Z are H and $R^4$ and $R^6$ are methyl;

(3) $R^4$ is not methyl or phenyl, when $R^2$, T, Y and Z are H, $R^6$ is methyl, and X and W are both chloro;

(4) W and Y are not both aryl; or (5) the compound is not

[Structure depicted: cyclohex-1-ene with CO2H at position 1, Me at position 4, and at position 6 both Me and phenyl substituents]

2. The compound of claim 1, wherein the compound is a compound of formula (Ia):

[Structure (Ia): cyclohexene ring with $R^2$, $R^1$, $R^4$, $R^6$ substituents and phenyl ring bearing T, W, X, Y, Z at positions 2, 3, 4, 5]

3. The compound of claim 1, wherein:
$R^1$ is selected from —COOH or —C(=O)NHSO$_2$R$^{12}$;
$R^2$ is H or C$_{1-2}$ alkyl;
$R^4$ is H, C$_{1-2}$ alkyl, C$_{1-2}$ alkoxy, or aryl wherein the C$_{1-2}$ alkyl, C$_{1-2}$ alkoxy and aryl may be optionally substituted with one or more $R^{4a}$'s;
$R^{4a}$ is independently —OH, C$_{1-4}$ alkoxy, —NHC(=O) C$_{1-6}$ alkyl, aryl, or aryloxy;
$R^6$ is selected from H, —OH or C$_{1-2}$ alkyl;
$R^{12}$ is C$_{1-2}$ alkyl, haloC$_{1-6}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-2}$ alkyl, C$_{1-2}$ alkoxy, or halo;
Y is H, C$_{1-2}$ alkyl, haloC$_{1-2}$ alkyl, halo or aryl;
Z is H;
or alternatively any two T, W, X, and Y can be taken together to form a fused cycloalkyl, heteroaryl, heterocyclyl ring, which may be optionally substitute with one or more $R^{4a}$'s.

4. The compound of claim 1, wherein:
$R^1$ is selected from —COOH or —C(=O)NHSO$_2$R$^{12}$;
$R^2$ is H or C$_{1-2}$ alkyl;
$R^4$ is H or C$_{1-2}$ alkyl, wherein the C$_{1-2}$ alkyl may be optionally substituted with one or more $R^{4a}$'s;
$R^{4a}$ is independently —OH, C$_{1-4}$ alkoxy, aryl, —NHC (=O)C$_{1-6}$ alkyl or aryloxy;
$R^6$ is selected from H or C$_{1-2}$ alkyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-2}$ alkyl, C$_{1-2}$ alkoxy, or halo;
Y is H, C$_{1-2}$ alkyl, haloC$_{1-2}$ alkyl, halo or aryl;
Z is H;
or alternatively any two T, W, X, and Y can be taken together to form a fused cycloalkyl, heteroaryl, heterocyclyl ring, which may be optionally substitute with one or more $R^{4a}$'s.

5. The compound of claim 1, wherein:
$R^1$ is selected from —COOH or —C(=O)NHSO$_2$R$^{12}$;
$R^2$ is H or C$_{1-2}$ alkyl;
$R^4$ is H or C$_{1-2}$ alkyl;
$R^6$ is C$_{1-2}$ alkyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-2}$ alkyl, C$_{1-2}$ alkoxy, or halo;
Y is H, C$_{1-2}$ alkyl, haloC$_{1-2}$ alkyl, halo or aryl;
Z is H;
or alternatively any two T, W, X, and Y can be taken together to form a fused cycloalkyl, heteroaryl, heterocyclyl ring.

6. The compound of claim 1, wherein:
$R^1$ is selected from —COOH or —C(=O)NHSO$_2$R$^{12}$;
$R^2$ is H or methyl;
$R^4$ is H or methyl;
$R^6$ is methyl;
$R^{12}$ is C$_{1-2}$ alkyl, haloC$_{1-2}$ alkyl or phenyl;
T is H, C$_{1-2}$ alkyl, haloC$_{1-2}$ alkyl, or C$_{1-2}$ alkoxy;
W is H, C$_{1-2}$ alkyl, haloC$_{1-2}$ alkyl, halo or aryl;
X is H, C$_{1-4}$ alkyl, C$_{1-4}$ alkoxy, or halo;
Y is H, C$_{1-2}$ alkyl, haloC$_{1-4}$ alkyl, halo or aryl;
Z is H;
or alternatively any two T, W, X, and Y can be taken together to form a fused cycloalkyl, heteroaryl, heterocyclyl ring.

7. The compound of claim 1, wherein:
$R^1$ is —COOH;
$R^2$ is H or methyl;
$R^4$ is H or methyl;
$R^6$ is methyl;
T is H, methyl, —CF$_3$, or methoxy;
W is H, methyl, —CF$_3$, Cl, F or phenyl;
X is H, C$_{1-2}$ alkyl, or halo;
Y is H, C$_{1-2}$ alkyl, haloC$_{1-4}$ alkyl, or halo;
Z is H;
or alternatively any two T, W, X, and Y can be taken together to form a fused cycloalkyl, heteroaryl, heterocyclyl ring.

8. The compound of claim 1, wherein:
$R^1$ is —COOH;
$R^2$ is H or methyl;
$R^4$ is H or methyl;
$R^6$ is methyl;
T is H, methyl, —CF$_3$, or methoxy;
W is H, methyl, —CF$_3$, Cl, F or phenyl;
X is H, methyl, Cl, or F;
Y is H, methyl, CF$_3$, Cl, F;
Z is H;
or alternatively any two T, W, X, and Y can be taken together to form a fused cycloalkyl, heteroaryl, heterocyclyl ring.

9. A compound or a stereoisomer or pharmaceutically acceptable salt thereof, wherein the compound is selected from:
6-(3,4-dichlorophenyl)-6-methylcyclohex-1-enecarboxylic acid,
6-(4-chlorophenyl)-6-methylcyclohex-1-enecarboxylic acid,
(4RS,6RS)-6-(3-phenylphenyl)-4,6-dimethylcyclohex-1-enecarboxylic acid,
(4RS,6RS)-6-(3-chloro-4-methylphenyl)-4,6-dimethylcyclohex-1-enecarboxylic acid,
(4RS,6RS)-6-(3,4-difluorophenyl)-4,6-dimethylcyclohex-1-enecarboxylic acid,
6-(2-methoxyphenyl)-6-methyl methylcyclohex-1-enecarboxylic acid,
6-(3,4-dimethylphenyl)-6-methylcyclohex-1-enecarboxylic acid, 6-(3-chlorophenyl)-6-methylcyclohex-1-enecarboxylic acid,
6-methyl-6-(3-(trifluoromethyl)-phenyl)cyclohex-1-enecarboxylic acid,
(4RS,6RS)-4,6-dimethyl-6-(3-(trifluoro-methyl)phenyl)cyclohex-1-enecarboxylic acid,
(4RS,6RS)-6-(4-chloro-3-(trifluoromethyl)-phenyl)-4,6-dimethylcyclohex-1-enecarboxylic acid,
(4RS,6RS)-6-(3,5-bis(trifluoromethyl)-phenyl)-4,6-dimethylcyclohex-1-enecarboxylic acid,
(4RS,6RS)-6-(3,4-dimethylphenyl)-4,6-dimethylcyclohex-1-enecarboxylic acid,
(4RS,6RS)-4,6-dimethyl-6-(napthalen-1-yl)cyclohex-1-enecarboxylic acid,
(4RS,6RS)-4,6-dimethyl-6-p-tolylcyclohex-1-enecarboxylic acid,
(4RS,6RS)-4,6-dimethyl-6-m-tolylcyclohex-1-enecarboxylic acid,
(4RS,6RS)-6-(2,3-dimethylphenyl)-4,6-dimethylcyclohex-1-enecarboxylic acid,
(4RS,6RS)-4,6-dimethyl-6-(naphthalen-2-yl)cyclohex-1-enecarboxylic acid,
(4RS,6RS)-6-(4-chlorophenyl)-4,6-dimethylcyclohex-1-enecarboxylic acid,
(4RS,6RS)-6-(4-fluorophenyl)-4,6-dimethylcyclohex-1-enecarboxylic acid,
(4RS,6RS)-6-(3-fluorophenyl)-4,6-dimethylcyclohex-1-enecarboxylic acid,
(4RS,6RS)-6-(4-fluoro-3-methylphenyl)-4,6-dimethylcyclohex-1-enecarboxylic acid,
(4RS,6RS)-6-(2,5-dimethylphenyl)-4,6-dimethylcyclohex-1-enecarboxylic acid,
(4RS,6RS)-6-(4-chloro-3,5-dimethylphenyl)-4,6-dimethylcyclohex-1-enecarboxylic acid,
(4RS,6RS)-4,6-dimethyl-6-(4-methyl-naphthalen-1-yl)cyclohex-1-enecarboxylic acid,
(4RS,6RS)-6-(3,5-dimethylphenyl)-4,6-dimethylcyclohex-1-enecarboxylic acid,
(4RS,6RS)-6-(3,5-dichlorophenyl)-4,6-dimethylcyclohex-1-enecarboxylic acid,
(4RS,6RS)-6-(3,4-dichlorophenyl)-4,6-dimethyl-N-(methylsulfonyl)cyclohex-1-enecarboxamide,
(4RS,6RS)-6-(3,4-dichlorophenyl)-4,6-dimethyl-N-(trifluoromethylsulfonyl)-cyclohex-1-enecarboxamide,
(4RS,6RS)-6-(3,4-dichlorophenyl)-4,6-dimethyl-N-(phenylsulfonyl)cyclohex-1-enecarboxamide,
(4S,6S)-6-(4-chloro-3-(trifluoromethyl)-phenyl)-4,6-dimethylcyclohex-1-enecarboxylic acid,
(4R,6R)-6-(4-chloro-3-(trifluoromethyl)phenyl)-4,6-dimethylcyclohex-1-enecarboxylic acid,
(4RS,6SR)-6-(3,4-dichlorophenyl)-6-hydroxy-2,4,-dimethylcyclohex-1-enecarboxylic acid,
(4RS,6RS)-6-(3,4-dichlorophenyl)-2,4,6-trimethylcyclohex-1-enecarboxylic acid,
(4RS,6RS)-6-(4-chloro-3-(trifluoromethyl)-phenyl)-4-(hydroxymethyl)-6-methylcyclohex-1-enecarboxylic acid,
(4RS,6RS)-6-(4-chloro-3-(trifluoromethyl)-phenyl)-4-(hydroxymethyl)-6-methylcyclohex-1-enecarboxylic acid,
(4RS,6RS)-4-(tert-butoxymethyl)-6-(4-chloro-3-(trifluoromethyl)phenyl)-6-methylcyclohex-1-enecarboxylic acid,
(4RS,6RS)-4-(acetamidomethyl)-6-(4-chloro-3-(trifluoromethyl)phenyl)-6-methylcyclohex-1-enecarboxylic acid, and
(4RS,6RS)-4-(benzyloxy)-6-(4-chloro-3-(trifluoromethyl)phenyl)-6-methylcyclohex-1-enecarboxylic acid.

10. A pharmaceutical composition comprised of a pharmaceutically acceptable carrier and a therapeutically effective amount of a compound of claim 1.

11. A pharmaceutical composition comprised of a pharmaceutically acceptable carrier and a therapeutically effective amount of a compound of claim 3.

12. A pharmaceutical composition comprised of a pharmaceutically acceptable carrier and a therapeutically effective amount of a compound of claim 4.

13. A pharmaceutical composition comprised of a pharmaceutically acceptable carrier and a therapeutically effective amount of a compound of claim 5.

14. A pharmaceutical composition comprised of a pharmaceutically acceptable carrier and a therapeutically effective amount of a compound of claim 6.

15. A pharmaceutical composition comprised of a pharmaceutically acceptable carrier and a therapeutically effective amount of a compound of claim 8.

16. A pharmaceutical composition comprised of a pharmaceutically acceptable carrier and a therapeutically effective amount of a compound of claim 9.

\* \* \* \* \*

UNITED STATES PATENT AND TRADEMARK OFFICE
CERTIFICATE OF CORRECTION

PATENT NO. : 8,507,559 B2
APPLICATION NO. : 13/003780
DATED : August 13, 2013
INVENTOR(S) : Percy H. Carter et al.

It is certified that error appears in the above-identified patent and that said Letters Patent is hereby corrected as shown below:

On the Title Page:

Item (75), Inventors:
Change "Gregory D. Brown, Landsdale, PA (US)" to -- Gregory D. Brown, Lansdale, PA (US) --.

Item (57), ABSTRACT:
Column 2, line 2 (Abstract), change "formula, (I)" to -- formula (I), --.
Column 2, line 8 (Abstract), change "formula, (I)" to -- formula (I) --.

Item (56), References Cited, under OTHER PUBLICATIONS:
Page 2, Column 2, line 50, Ishizuka, N. et al. reference, line 3, change "dioxo1" to -- dioxol --.
Page 3, Column 2, line 59, Sprague, P.W. et al. reference, line 2, change "methy1-5-*H*" to -- methyl-5*H* --.

In the Claims:

Claim 8:
Column 62, line 39, change "$R^{1}$" to -- $R^1$ --.

Claim 9:
Column 63, line 35, change "naphthalen-l-yl)" to -- naphthalen-1-yl) --.
Column 64, line 5, change "(4RS,6SR)" to -- (4RS,6RS) --.
Column 64, lines 5 and 6, change "2,4,-dimethylcyclohex" to -- 2,4-dimethylcyclohex --.

Signed and Sealed this
First Day of April, 2014

Michelle K. Lee
*Deputy Director of the United States Patent and Trademark Office*